United States Patent
Kovi et al.

(10) Patent No.: US 9,493,473 B2
(45) Date of Patent: Nov. 15, 2016

(54) PROCESSES FOR MAKING PONATINIB AND INTERMEDIATES THEREOF

(71) Applicant: Apicore US LLC, Somerset, NJ (US)

(72) Inventors: Ravishanker Kovi, Monroe, NJ (US); Jayaraman Kannapan, Gujarat (IN); Sanjay F. Thakor, Gujarat (IN); Rajesh A Patel, North Gujarat (IN)

(73) Assignee: Apicore US LLC, Somerset, NJ (US)

( * ) Notice: Subject to any disclaimer, the term of this patent is extended or adjusted under 35 U.S.C. 154(b) by 0 days.

(21) Appl. No.: 14/984,446

(22) Filed: Dec. 30, 2015

(65) Prior Publication Data

US 2016/0108053 A1  Apr. 21, 2016

Related U.S. Application Data

(63) Continuation of application No. 14/279,607, filed on May 16, 2014.

(60) Provisional application No. 61/824,070, filed on May 16, 2013.

(51) Int. Cl.

| | | |
|---|---|---|
| *C07D 487/04* | (2006.01) | |
| *C07D 209/48* | (2006.01) | |
| *C07C 233/80* | (2006.01) | |
| *C07C 233/75* | (2006.01) | |
| *C07C 233/76* | (2006.01) | |
| *C07D 233/80* | (2006.01) | |
| *C07D 233/76* | (2006.01) | |

(52) U.S. Cl.
CPC ........... *C07D 487/04* (2013.01); *C07C 233/75* (2013.01); *C07C 233/76* (2013.01); *C07C 233/80* (2013.01); *C07D 209/48* (2013.01)

(58) Field of Classification Search
None
See application file for complete search history.

(56) References Cited

U.S. PATENT DOCUMENTS

| 8,114,874 B2 | 2/2012 | Zou |
| 8,278,307 B2 | 10/2012 | Shakespeare |
| 2007/0191376 A1 | 8/2007 | Zou |
| 2013/0053370 A1 | 2/2013 | Son |
| 2014/0343282 A1 | 11/2014 | Kovi |

FOREIGN PATENT DOCUMENTS

| WO | 2004108699 A1 | 12/2004 |
| WO | 2007075869 A2 | 7/2007 |
| WO | 2011053938 A1 | 5/2011 |
| WO | 2012139027 A1 | 10/2012 |

OTHER PUBLICATIONS

Office Action for related U.S. Appl. No. 14/279,607, dated May 16, 2014.
International Search Report and Written Opinion for corresponding PCT application No. PCT/2016/36857, 9 pages, dated Sep. 7, 2016.
Gamble, et al. "Aryl Nitro Reduction with Iron Powder or Stannous Chloride under Ultrasonic Irradiation", Synthetic communications, 37,2007, 2777-2786; University of Wollongong-Research Online, pp. 1-12 (2007).

*Primary Examiner* — Emily Bernhardt
(74) *Attorney, Agent, or Firm* — Timothy X. Gibson, Esq.; Gibson & Dernier LLP

(57) ABSTRACT

Novel synthetic approaches to make 3-(imidazo[1,2-b]pyridazin-3-ylethynyl)-4-methyl-N-[4-[(4-methylpiperazin-1-yl)methyl]-3-(trifluoromethyl)phenyl]benzamide, intermediates and pharmaceutically acceptable salts thereof are provided.

8 Claims, No Drawings

PROCESSES FOR MAKING PONATINIB AND INTERMEDIATES THEREOF

CROSS-REFERENCE TO RELATED APPLICATIONS

This application is a continuation of U.S. patent application Ser. No. 14/279,607 filed May 16, 2014 which claims the benefit of U.S. Provisional Patent Application No. 61/824,070, filed May 16, 2013, the entireties of which are incorporated herein by reference.

FIELD OF THE INVENTION

The presently disclosed subject matter provides novel synthetic approaches to make 3-(imidazo[1,2-b]pyridazin-3-ylethynyl)-4-methyl-N-[4-[(4-methylpiperazin-1-yl)methyl]-3-(trifluoromethyl)phenyl]benzamide, intermediates and pharmaceutically acceptable salts thereof.

BACKGROUND 3-(imidazo[1,2-b]pyridazin-3-ylethynyl)-4-methyl-N-[4-[(4-methylpiperazin-1-yl)methyl]-3-(trifluoromethyl)phenyl]benzamide, also known as ponatinib, is a multi-targeted tyrosine-kinase inhibitor used in the treatment of chronic myeloid leukemia (CML) and Philadelphia chromosome positive (Ph+) acute lymphoblastic leukemia (ALL). Some forms of CML, those that have the T315I mutation, are resistant to current therapies such as imatinib. Ponatinib was designed to be effective against these types of tumors.

SUMMARY OF THE INVENTION

There are few synthetic approaches available for the preparation of ponatinib. Some examples are found in U.S. Pat. Nos. 8,114,874 and 8,278,307, PCT 2012139027, PCT 2011053938 and PCT 2007075869. Regardless of the synthetic methodology used, the process requires modifications and improvement to make it a commercially economical and easily scalable method.

Prior art approaches for making ponatinib make use of the Sonogarshira coupling of the acetylenic moiety with other two aromatic systems and alternatively the aromatic systems are coupled together and then reacted with the acetylenic moiety. More importantly the piperazine moiety of the drug is introduced by the reaction of the halides of the precursor moiety with N-methyl piperazine by conventional condensation methods. This method of making ponatinib is cumbersome and involves a synthesis of more than 20 steps. Thus, there is a need to make the drug by a simpler and easily scalable process.

The presently disclosed processes involve a novel synthetic approach to make ponatinib in a simple and easily scalable process, overcoming the drawbacks of prior art processes.

In one embodiment a method is disclosed for the production of ponatinib hydrochloride of the formula (I)

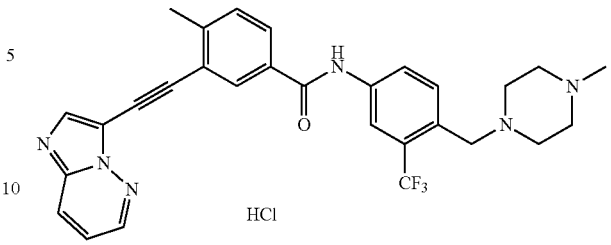

including reacting a compound of formula (II) 1-(halomethyl)-4-nitro-2-(trifluoromethyl)benzene wherein X is a halogen, with potassium phthalimide to obtain a phthalimide derivative, reducing the phthalimide derivative, reacting the reduced phthalimide derivative with 3-iodo-4-methylbenzoyl chloride having the formula (IV)

to form an amide, reacting the amide with 3-ethynylimidazo[1,2-b]pyridazine of the formula (V)

in a coupling reaction, subjecting a product of the coupling reaction to hydrolysis to obtain N-(4-(aminomethyl)-3-(trifluoromethyl)phenyl)-3-(imidazo[1,2-b]pyridazin-3- ylethynyl)-4-methylbenzamide, subsequently forming a piperazine ring by treatment of the N-(4-(aminomethyl)-3-(trifluoromethyl)phenyl)-3-(imidazo[1,2-b]pyridazin-3-yl-ethynyl)-4-methylbenzamide with a) 2-chloro-N-(2-chloroethyl)-N-methylethanamine; or b) a 2-chloro-N-(2-chloroethyl)-N-substituted derivative of the formula (VI)

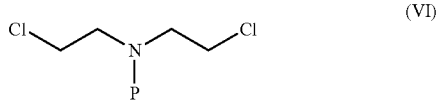

(VI)

wherein P is a protecting group and subsequently deprotecting the piperazine ring; and forming the ponatinib hydrochloride using hydrogen chloride.

In one embodiment X may be bromine. In another embodiment, P may be $CH_3$, tosyl, mesyl, carboxybenzyl, benzyl or amino. In a further embodiment the step of deprotecting the piperazine ring may include N-methylation with methyl iodide.

The step of deprotection of the piperazine ring may be carried out in an acid, base and under hydrogenation conditions. The acid may be for example concentrated sulfuric acid, HBr in acetic acid, HBr in water and trifluoroacetic acid.

Hydrogenation may be carried out using hydrogen pressure and a catalyst. The catalyst may be for example palladium and/or Raney nickel.

In another embodiment, a method of making ponatinib hydrochloride having the formula (I) includes reacting a 4-substituted-3-(trifluoromethyl) analogue having the formula (VIII)

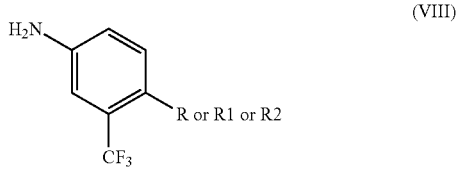

(VIII)

wherein R is CN, R1 is COOR", R2 is $CH_2N_3$ and R" is $CH_3$, $C_2H_5$ or a higher homologue, with 3-iodo-4-methyl-benzoic acid of formula (IV)

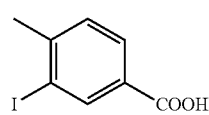

(IV)

to obtain an amide of the formula (IIa)

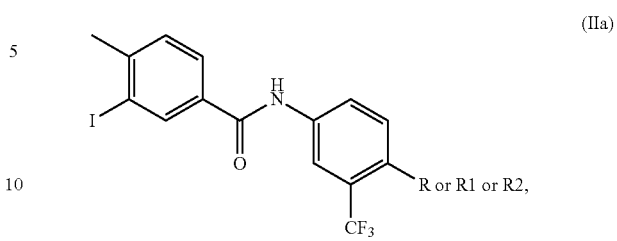

(IIa)

coupling the amide of formula IIa via reaction with 3-ethynylimidazo[1,2-b]pyridazine having the formula (V)

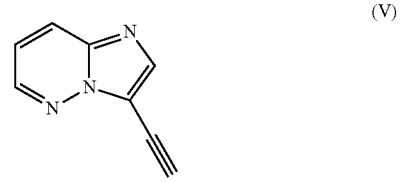

(V)

to obtain a compound of the formula (IIe)

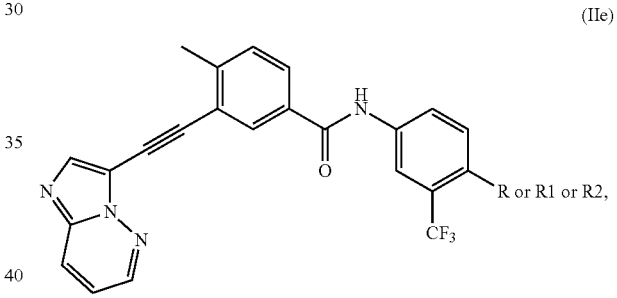

(IIe)

subjecting the compound of formula (IIe) to reaction conditions to obtain a compound of formula (IIf), wherein the conditions may include reduction when R is CN, esterification when R is COOH, and reduction, halogenation and azide formation and reduction of the azide when R is COOR

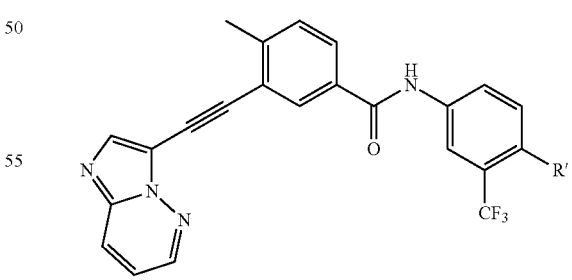

wherein R' is $CH_2NH_2$ or $CH_2OH$, forming a piperazine ring via reaction of the compound of formula (IIf) with a) 2-chloro-N-(2-chloroethyl)-N-methylethanamine; or b) 2-chloro-N-(2-chloroethyl)-N-substituted derivative of the formula (VI)

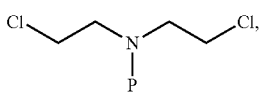

wherein P is a protecting group and subsequently deprotecting the piperazine ring; and forming the ponatinib hydrochloride using hydrogen chloride. In one embodiment P may be $CH_3$, tosyl, mesyl, carboxybenzyl, benzyl or amino. The step of deprotecting the piperazine ring may includes N-methylation with methyl iodide.

In one embodiment esterification may be carried out using sodium borohydride and lithium aluminium hydride. Halogenation may be carried out using thionyl chloride, phosphorous oxychloride, or phosphorous trichloride. Azide formation may be carried out using a metal azide such as sodium azide. Azide reduction may be carried out using palladium and hydrogen.

In another embodiment, a method of making ponatinib hydrochloride having the formula (I) includes reacting 4-amino-2-(trifluoromethyl)benzaldehyde having the formula (IX)

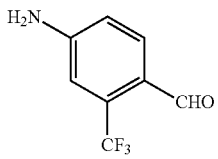

with 3-ethynyl-4-methyl benzoic acid of formula (VII)

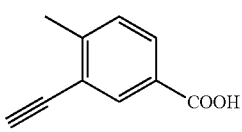

to obtain N-(4-formyl-3-(trifluoromethyl)phenyl)-3-iodo-4-methylbenzamide having the formula (IIIa)

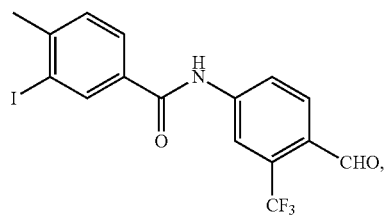

coupling the compound of formula (IIIa) with a compound having the formula (V)

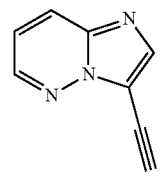

to obtain a compound having the formula (IIIb)

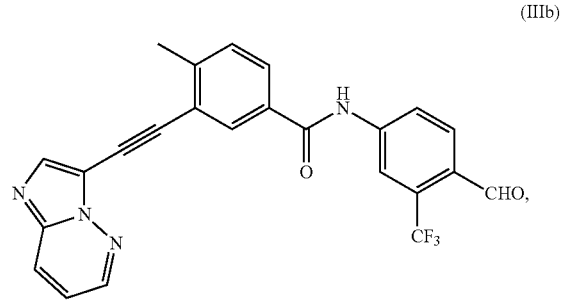 [SMILES: Cc1ccc(C(=O)Nc2ccc(C=O)c(C(F)(F)F)c2)cc1C#Cc1cnc2cccnn12]

subjecting the compound of formula (IIIb) to reductive amination with N-methyl piperazine to obtain compound having the formula (IIIc)

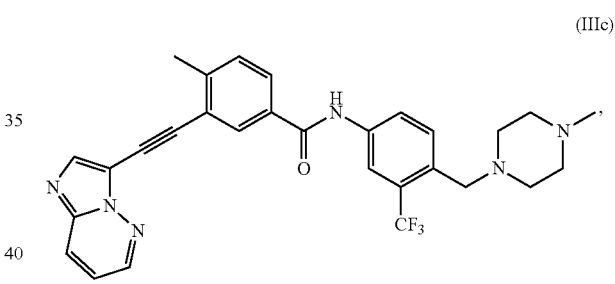

and subjecting the compound of formula (IIIc) to hydrogen chloride to obtain the ponatinib hydrochloride.

In one embodiment, the reductive amination may be carried out using a base and an organic solvent. The base may be selected for example from sodium cyanoborohydride and sodium triacetoxyborohydride. The solvent may be selected for example from acetic acid, isopropyl alcohol, methanol, ethanol and n-butanol.

In a still further embodiment, a method of making ponatinib hydrochloride having the formula (I) includes reacting a 4-substituted-3-(trifluoromethyl) analogue having the formula (VIII)

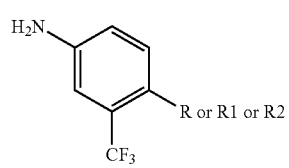

wherein R is CN, R1 is COOR", R2 is $CH_2N_3$ and R" is $CH_3$, $C_2H_5$ or a higher homologue thereof, with 3-ethynyl-4-methylbenzoic acid of formula (VII)

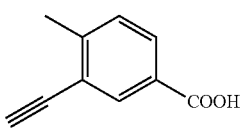
(VII)

to obtain a compound having the formula (IVa)

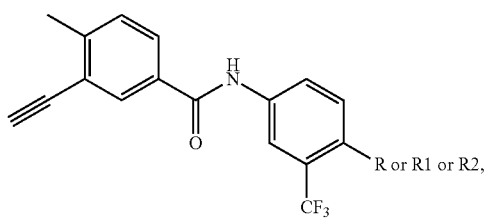
IVa subjecting the compound of formula (IVa) to treatment with a catalyst to obtain N-(4-(R'-substituted)-3-(trifluoromethyl)phenyl)-3-ethynyl-4-methylbenzamide of the formula (IVb)

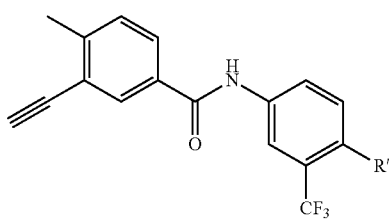
(IVb)

wherein R' is $CH_2NH_2$ or $CH_2OH$, forming a piperazine ring by reacting the compound of formula (IVb) with either
a) 2-chloro-N-(2-chloroethyl)-N-methylethanamine; or
b) 2-chloro-N-(2-chloroethyl)-N-substituted derivative having the formula (VI)

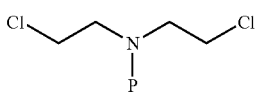
(VI)

wherein P is a protecting group and subsequently deprotecting the piperazine ring; and forming the ponatinib hydrochloride using hydrogen chloride.

In an embodiment P may be $CH_3$, mesyl, tosyl, carboxybenzyl, benzyl or nitrobenzyl. The step of forming the piperazine ring may include using substituted a 2-chloro-N-(2-chloroethyl)-N-substituted (VII) derivative in an organic solvent and a base. Deprotection of the piperazine ring may be carried out in an acid, base and under hydrogenation conditions. The acid may be selected for example from concentrated sulfuric acid, HBr in acetic acid and HBr in water. Hydrogenation may be carried out with hydrogen pressure and a catalyst. Examples of suitable catalysts include palladium and/or Raney Nickel.

In accordance with yet a further embodiment, a method of making ponatinib hydrochloride having the formula (I) includes reacting 4-amino-2-(trifluoromethyl)benzaldehyde having the formula (IX)

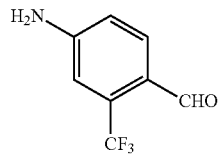
(IX)

with 3-ethynyl-4-methylbenzoic acid having the formula (VII)

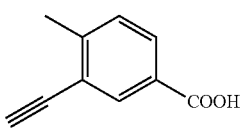
(VII)

to obtain 3-ethynyl-N-(4-formyl-3-(trifluoromethyl)phenyl)-4-methylbenzamide having the formula (Va)

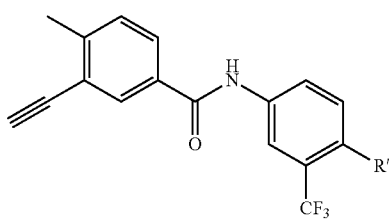
Va subjecting the compound of formula (Va) to treatment with sodium triacetoxyborohydride and N-methylpiperazine to obtain 3-ethynyl-4-methyl-N-(4-((4-methylpiperazin-1-yl)methyl)-3-(trifluoromethyl)phenyl)benzamide having the formula (Vb)

Vb subjecting the compound of formula (Vb) to reactive coupling with 3-ethynylimidazo[1,2-b]pyridazine having the formula (V)

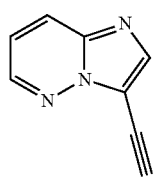
(V)

to obtain a resulting product, subjecting the resulting product to reductive amination with N-methyl piperazine, and forming the ponatinib hydrochloride using hydrogen chloride.

In accordance with further embodiments, novel intermediates are provided. The following are examples of such novel intermediates:

N-(4-((1,3-dioxoisoindolin-2-yl)methyl)-3-(trifluoromethyl)phenyl)-3-iodo-4-methylbenzamide having the formula

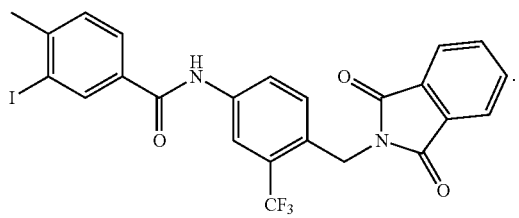 [SMILES: Cc1ccc(C(=O)Nc2ccc(CN3C(=O)c4ccccc4C3=O)c(C(F)(F)F)c2)cc1I]

N-(4-(R'-substituted)-3-(trifluoromethyl)phenyl)-3-(imidazo[1,2-b]pyridazin-3-ylethynyl)-4-methylbenzamide having the formula

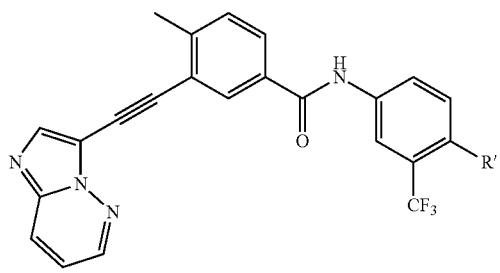

wherein R' is CH$_2$NH$_2$ or CH$_2$OH.

N-(4-formyl-3-(trifluoromethyl)phenyl)-3-(imidazo[1,2-b]pyridazin-3-ylethynyl)-4-methylbenzamide having the formula

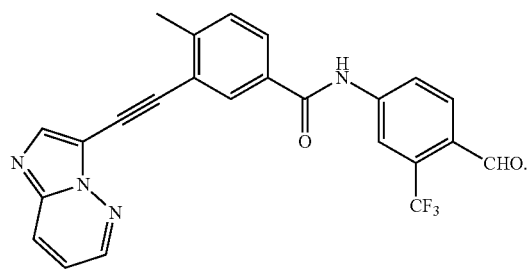 [SMILES: Cc1ccc(C(=O)Nc2ccc(C=O)c(C(F)(F)F)c2)cc1C#Cc1cnc2cccnn12]

3-ethynyl-N-(4-(substituted)-3-(trifluoromethyl)phenyl)-4-methylbenzamide having the formula

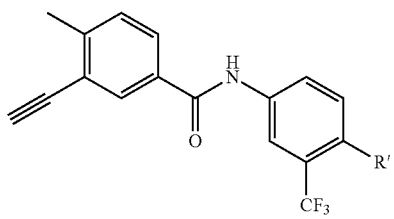

wherein R' is CH$_2$NH$_2$ or CH$_2$OH.

3-ethynyl-N-(4-formyl-3-(trifluoromethyl)phenyl)-4-methylbenzamide having the formula

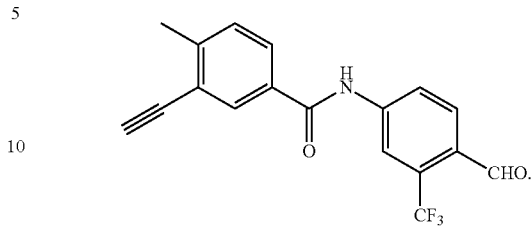

Given above is a simplified summary in order to provide a basic understanding of some aspects described herein. This summary is not an extensive overview, and is not intended to identify key/critical elements or to delineate the scope of the claimed subject matter.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

The following description describes novel synthetic schemes which provide economical and easily scalable methods for making the drug ponatinib at a commercial scale. Methods of preparation as described herein may involve the formation of a piperazine ring by a novel and simple method of condensing the aromatic amine moiety with commercially available materials 2-chloro-N-(2-chloroethyl)-N-methylethanamine or N-protected 2-chloro-N-(2-chloroethyl)amine. The presently disclosed methods are so efficient that ponatinib may be produced thereby in only six to seven synthetic steps, drastically reducing manufacturing complexity and demands compared to prior art methods.

Intermediates as disclosed herein are novel and prepared by simple, scalable methods which are user friendly and highly reproducible even at a very large scale.

The following embodiments of novel schemes I-V are provided.

SCHEME-I
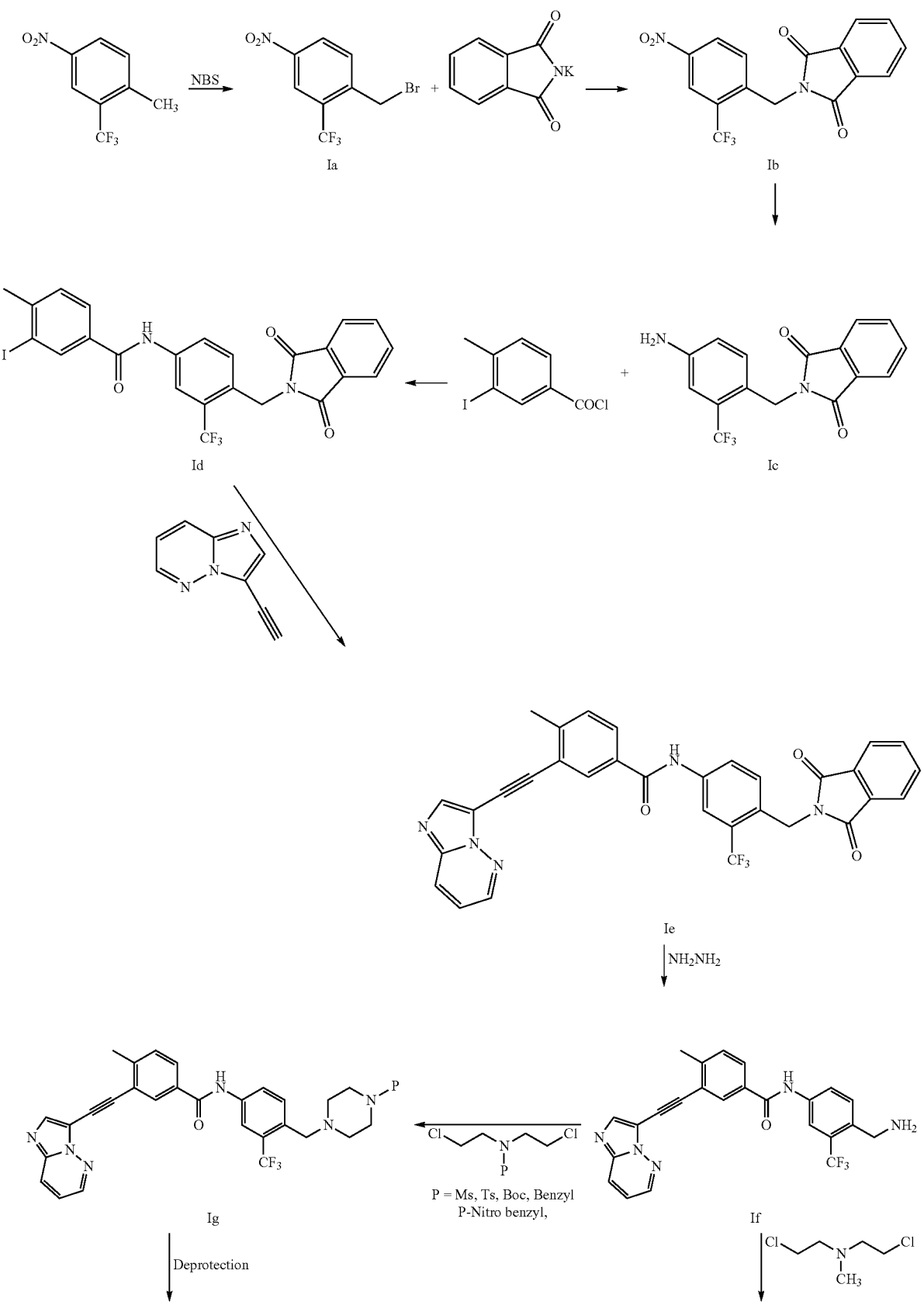

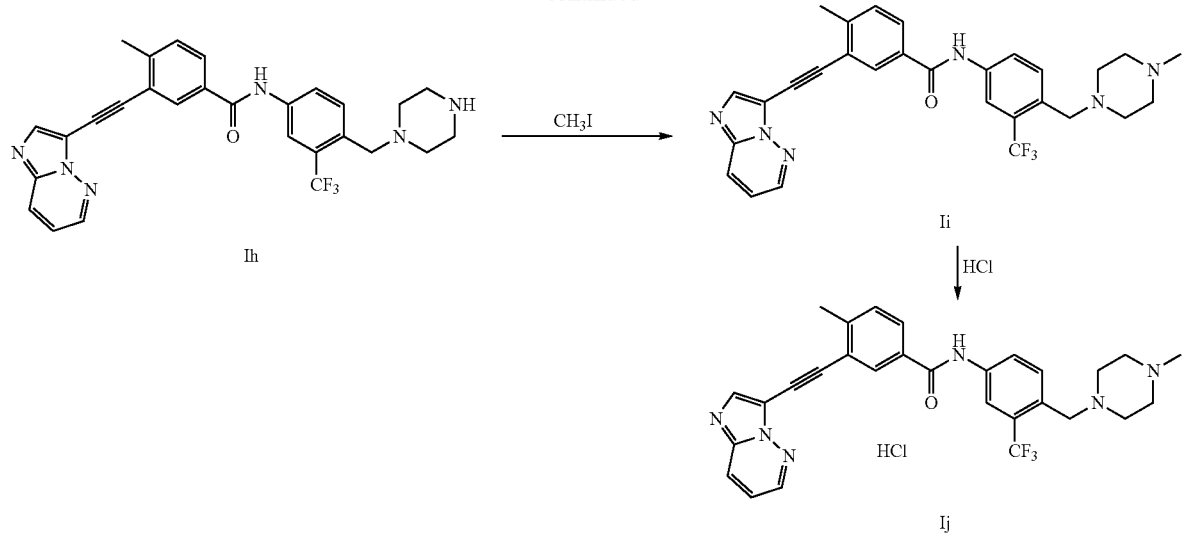

Scheme-I

In accordance with one embodiment for making ponatinib, commercially available methyl-4-nitro-2-(trifluoromethyl)benzene is converted to 1-(chloromethyl) or 1-(bromomethyl)-3-(trifluoromethyl) aniline with N-bromo succinimide or with N-chloro succinimide. The product is then reduced with palladium carbon under hydrogenation conditions to 4-(bromomethyl)-3-(trifluoromethyl) aniline or 4-(chloromethyl)-3-(trifluoromethyl) aniline. This aniline derivative is protected with a phthalimide derivative and the subsequent amide formation subjected to Sonogarshira reactions. This method of phthalimide protection helps improve yield of further reactions by controlling side reactions which are prone to take place when using conventional methods. Protection of the phthalimide group helps in introducing the required amine moiety of the molecule by a simple deprotection mechanism.

The formation of the piperazine ring of ponatinib may be achieved by the novel method of coupling the amino group with 2-chloro-N-(2-chloroethyl)-N-methylethanamine or by coupling with N-protected 2-chloro-N-(2-chloroethyl)amine followed by deprotection and N-methylation with methyl iodide. The above method of coupling helps in improving the quality of the final product with an improved yield.

In one embodiment, a method for the production of ponatinib hydrochloride (I) of the formula

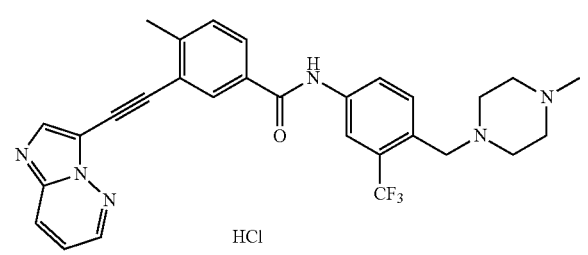

(I)

includes reacting 1-(halo methyl)-4-nitro-2-(trifluoromethyl)benzene (II) with potassium phthalimide (III) to obtain a phthalimide derivative, reducing the phthalimide derivative, reacting the phthalimide derivative with 3-iodo-4-methylbenzoyl chloride (IV) to form an amide, reacting the amide with 3-ethynylimidazo[1,2-b]pyridazine (V) in a coupling reaction, subjecting the product of the coupling reaction to hydrolysis to obtain N-(4-(aminomethyl)-3-(trifluoromethyl)phenyl)-3-(imidazo[1,2-b]pyridazin-3-ylethynyl)-4-methylbenzamide, subsequently forming a piperazine ring by treatment of the N-(4-(aminomethyl)-3-(trifluoromethyl)phenyl)-3-(imidazo[1,2-b]pyridazin-3-ylethynyl)-4-methylbenzamide with a) 2-chloro-N-(2-chloroethyl)-N-methylethanamine or b) with a 2-chloro-N-(2-chloroethyl)-N-substituted derivative (VI), deprotecting the piperazine ring, and forming the ponatinib hydrochloride using hydrochloric acid.

Species (II)-(VI) are shown below:

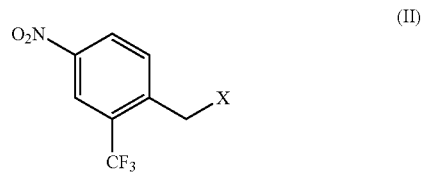

X = Halogens

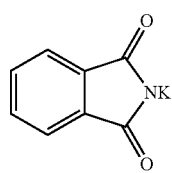

Potassium phthalimide

-continued
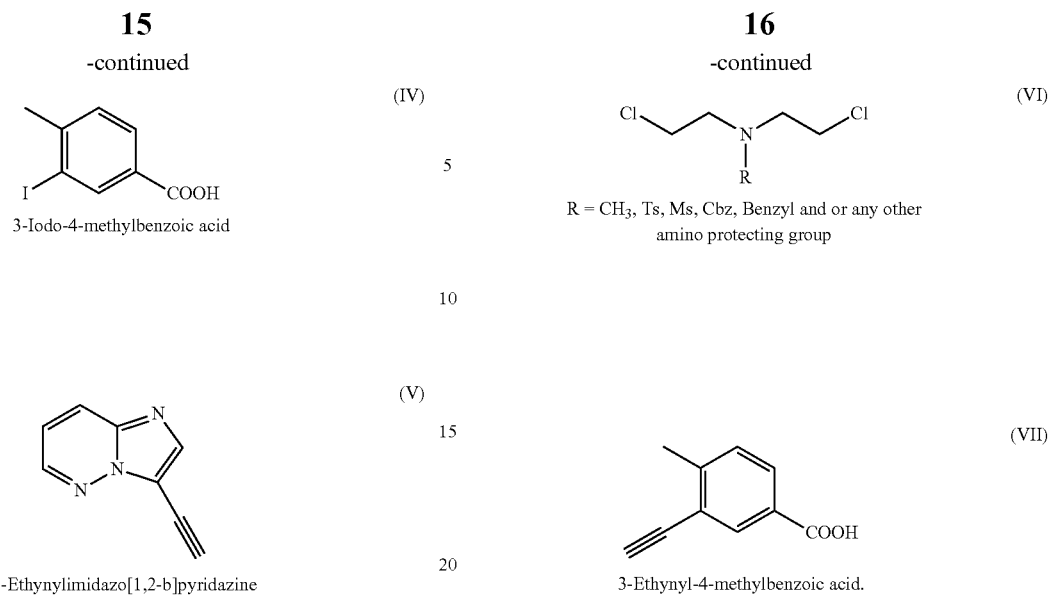
(IV) 3-Iodo-4-methylbenzoic acid
(V) 3-Ethynylimidazo[1,2-b]pyridazine
(VI) R = CH₃, Ts, Ms, Cbz, Benzyl and or any other amino protecting group
(VII) 3-Ethynyl-4-methylbenzoic acid.
SCHEME-II
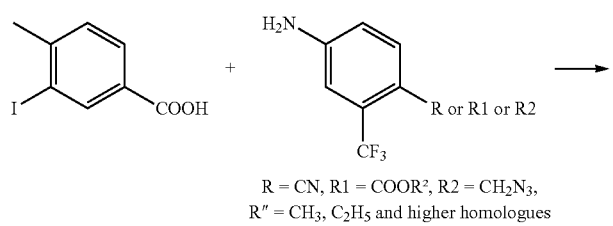
R = CN, R1 = COOR², R2 = CH₂N₃,
R″ = CH₃, C₂H₅ and higher homologues
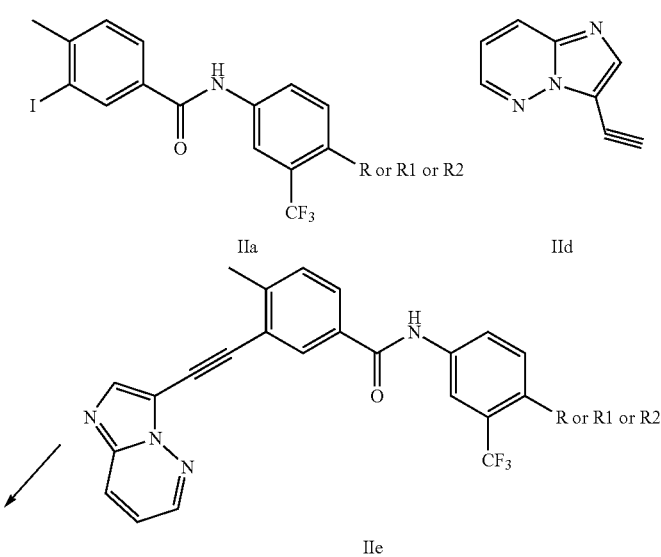
IIa  IId
IIe

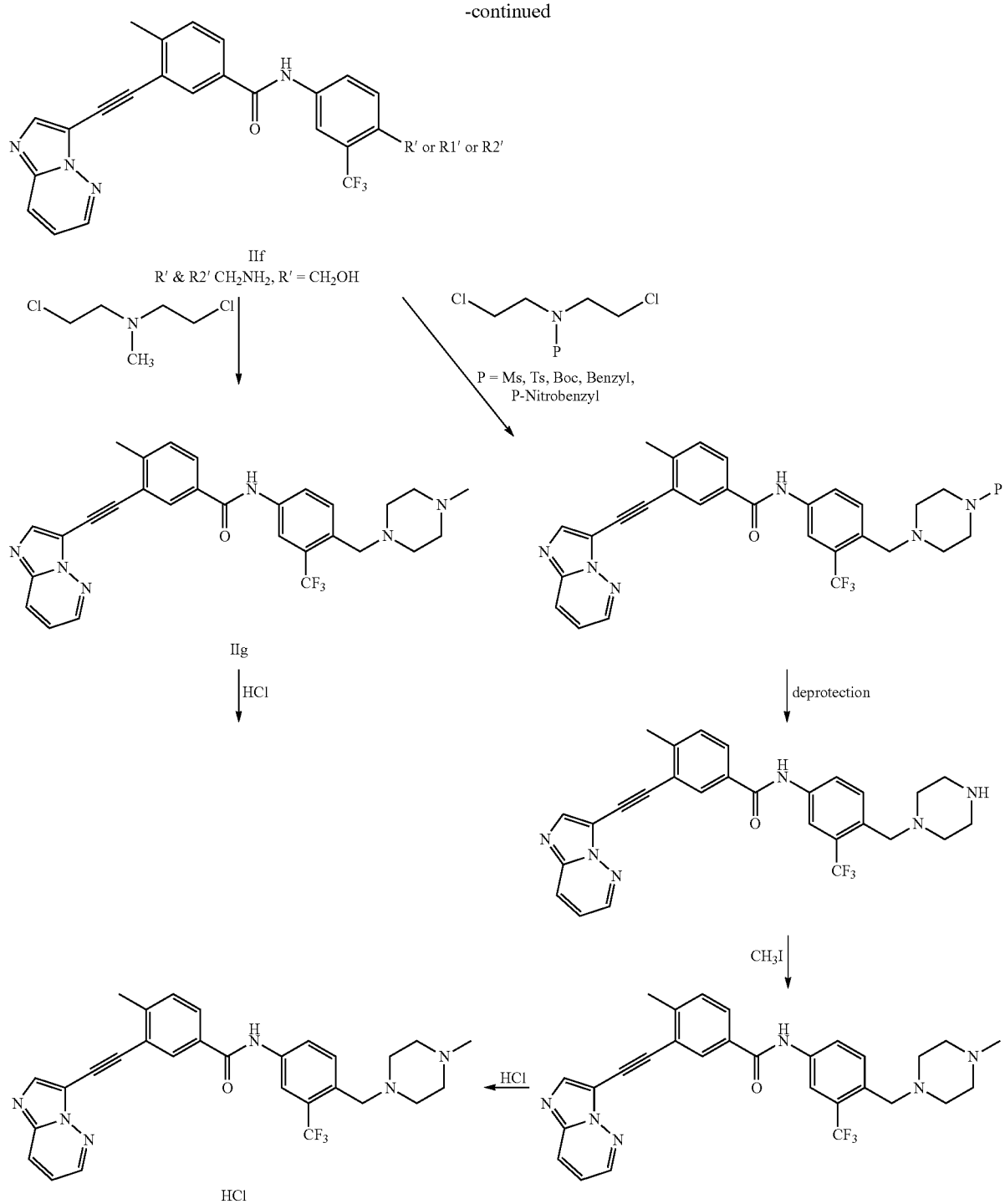

Scheme-II

In accordance with another embodiment, another method of making ponatinib employs the commercially inexpensive raw material 4-amino-2-(trifluoromethyl)benzonitrile. The nitrile group can be converted to amine by simple reduction/hydrogenation methods with an inexpensive catalyst such as Raney® nickel. The resultant amine can be easily cyclized to a piperazine derivative by the above methods.

Commercially available methyl 3-iodo-4-methylbenzoate and ethyl 3-iodo-4-methyl benzoate can be converted to their corresponding alcohols which, which may then be converted to their corresponding alkyl chlorides. The alkyl chlorides may then be cyclized to the required piperazine moiety by 2-chloro-N-(2-chloroethyl)-N-protected amines or with 2-chloro-N-(2-chloroethyl)-N-methylethanamine.

In one embodiment ponatinib hydrochloride (I) may be prepared by the formation of an amide such as N-(4-cyano-3-(trifluoromethyl)phenyl)-3-iodo-4-methylbenzamide by reaction of 4-substituted-3-(trifluoromethyl) analogues (VIII)

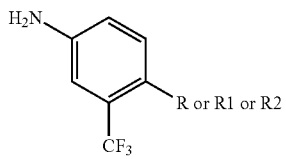

R = CN, R1 = COOR″, R2 = CH₂N₃,
R″ = CH₃, C₂H₅ and higher homologues (VIII)

with compound (IV), subsequent coupling of the amide via reaction with compound (V), subsequent reduction (if R=CN in compound VIII), esterification (if R=COOH), or reduction, halogenation and azide formation and reduction of the azide (if R=COOR), forming a piperazine ring via reaction with a) 2-chloro-N-(2-chloroethyl)-N-methylethanamine or b) with 2-chloro-N-(2-chloroethyl)-N-substituted (VI) derivatives, followed by deprotection, and hydrochloride formation via reaction with hydrochloric acid.

SCHEME-III

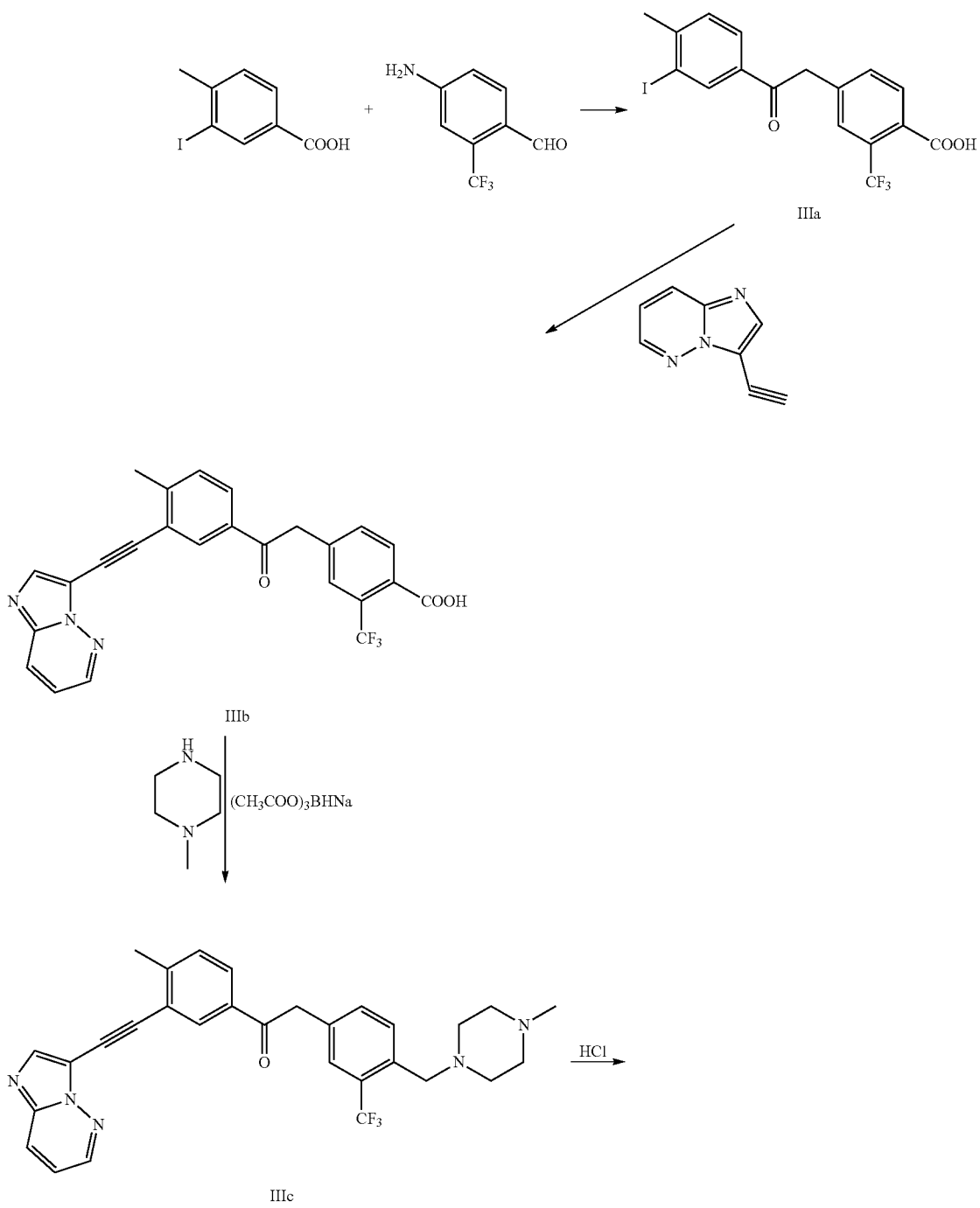

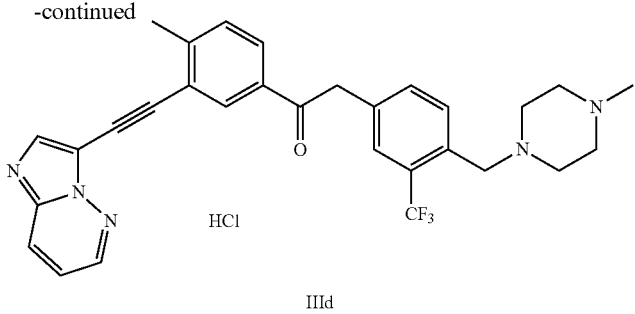

IIId

Scheme III

In accordance with yet another embodiment, a further method of making ponatinib is provided wherein 3-iodo-4-methylbenzoic acid is condensed with 4-amino-2-(trifluoromethyl)benzaldehyde to form an amide which is further condensed with 3-ethynylimidazo[1,2-b]pyridazine and the coupled product is directly condensed with N-methylpiperazine by a reductive amination process. This method of making the piperazine moiety is simple, reproducible and novel.

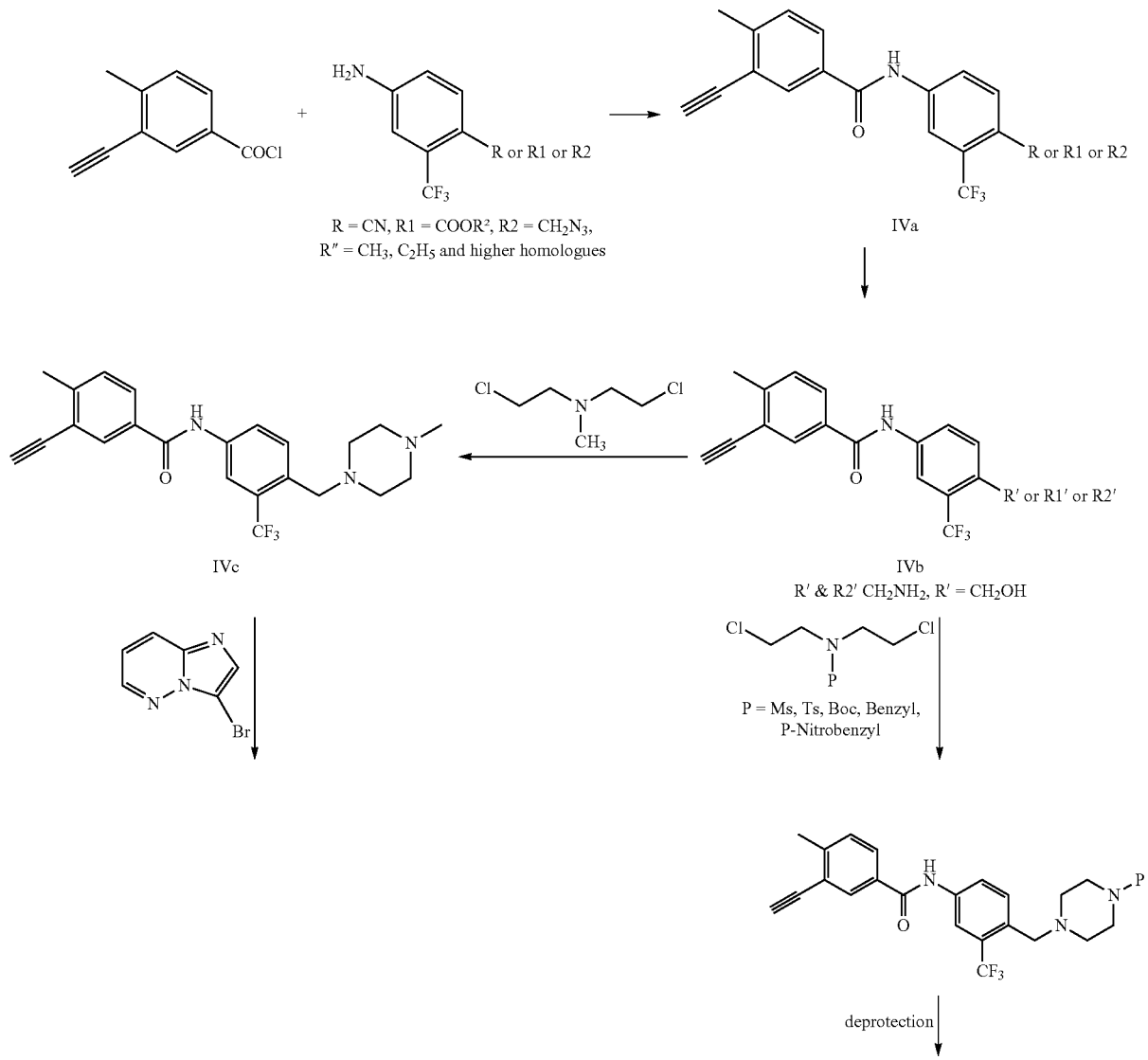

SCHEME-IV 23 24

-continued

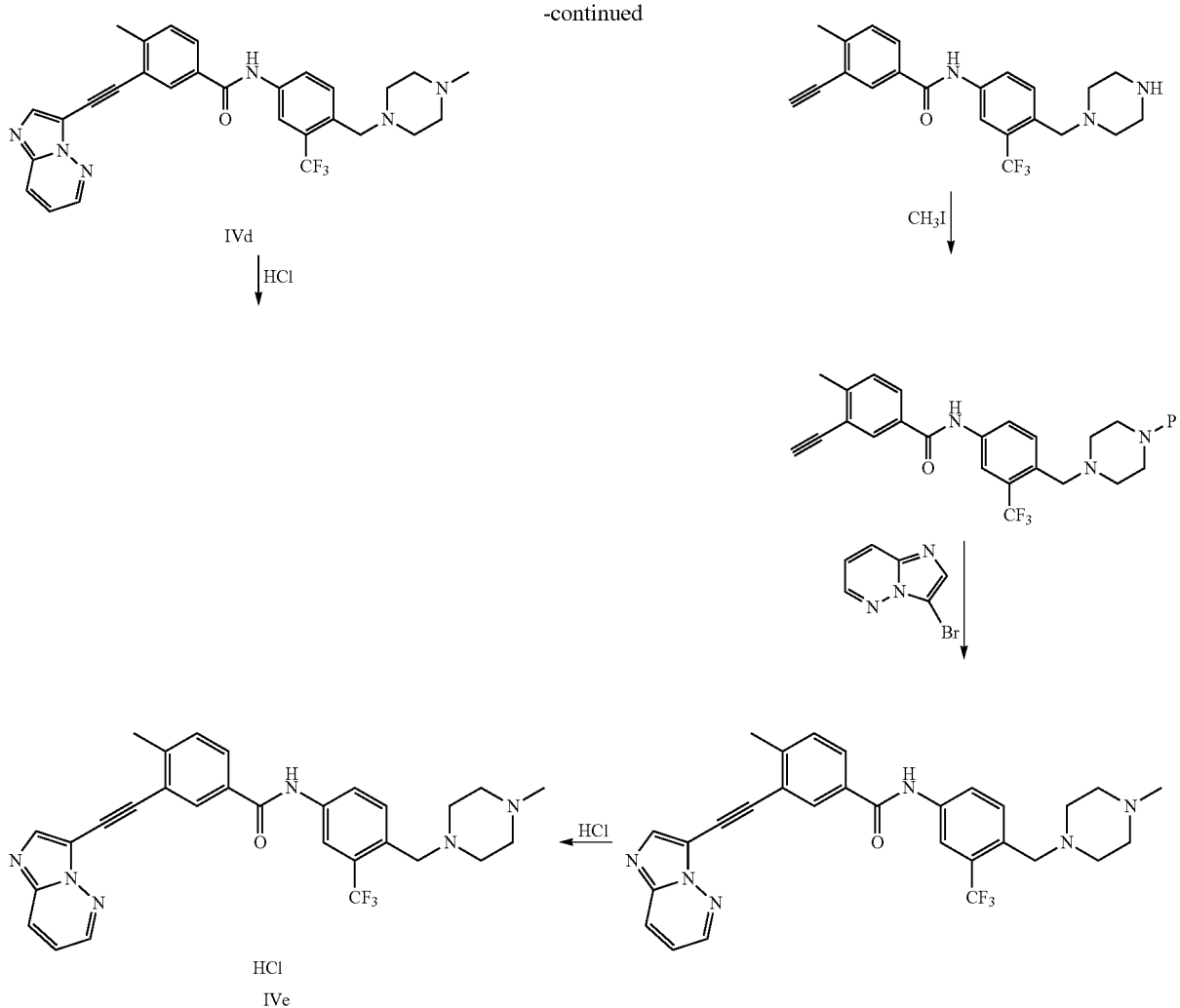

Scheme IV

In accordance with a further embodiment, another method of making ponatinib is provided wherein the 3-ethynyl-4-methylbenzoic acid is condensed with trifluoro substituted aniline derivatives and the resultant amide is cyclized with the 2-chloro-N-(2-chloroethyl)-N-protected amines or with 2-chloro-N-(2-chloroethyl)-N-methylethanamine to form the piperazine ring.

SCHEME-V

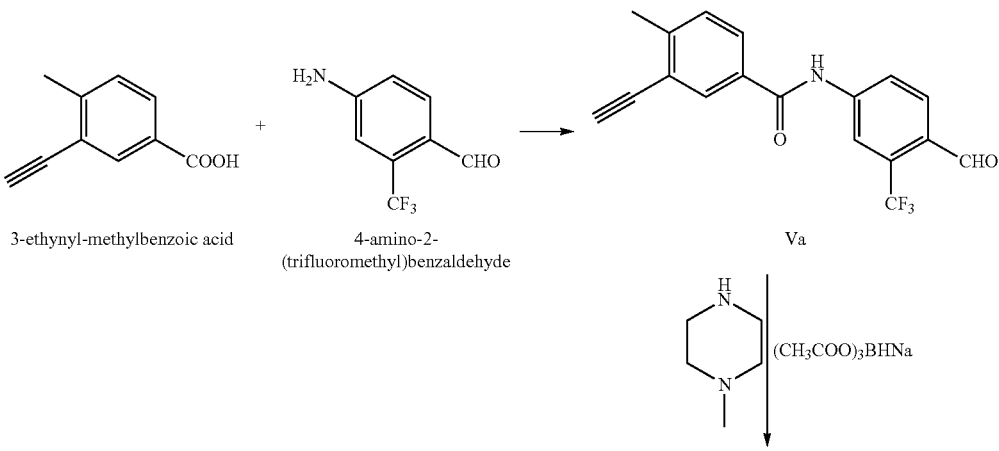

3-ethynyl-methylbenzoic acid    4-amino-2-(trifluoromethyl)benzaldehyde    Va

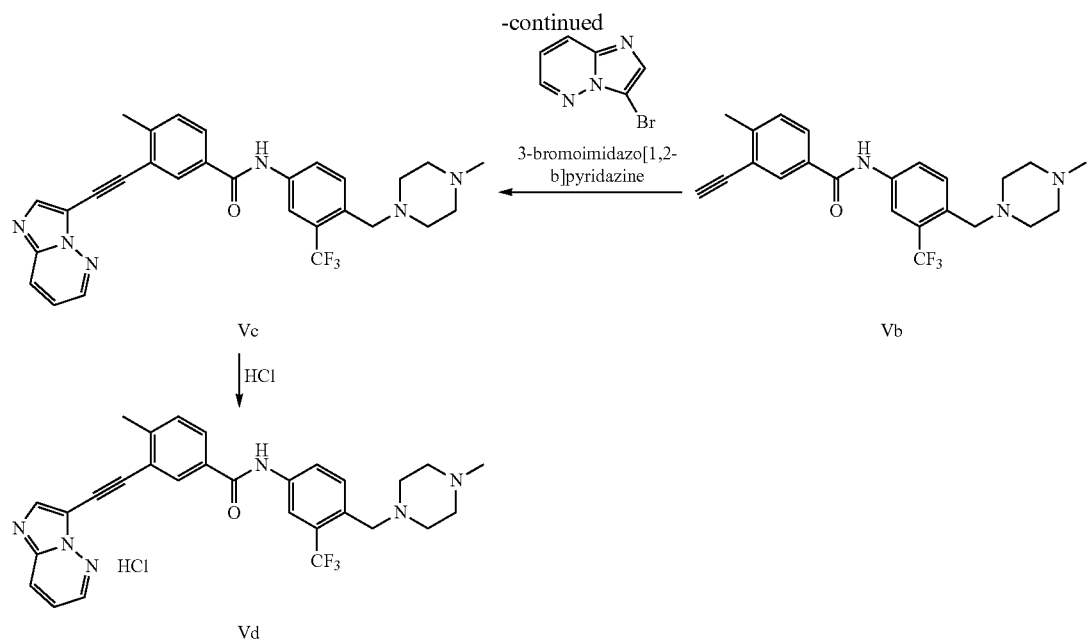

Scheme V

In still a further embodiment, scheme (V) involves a novel method of making ponatinib hydrochloride by condensing 3-ethynyl-4-methylbenzoic acid 4-amino-2-(trifluoromethyl)benzaldehyde reductively aminating the resultant amide with N-methyl piperazine using sodium cyanoborohydride or sodium triacetoxy borohydride. The formed piperazine moiety is condensed with the 3-bromoimidazo[1,2-b]pyridazine to obtain ponatinib free base which may be converted to hydrochloride by any known process of making hydrochlorides.

Examples and Experiments

The following are examples of process conditions and reagents that may be employed in connection with Schemes I-V.

SCHEME-I

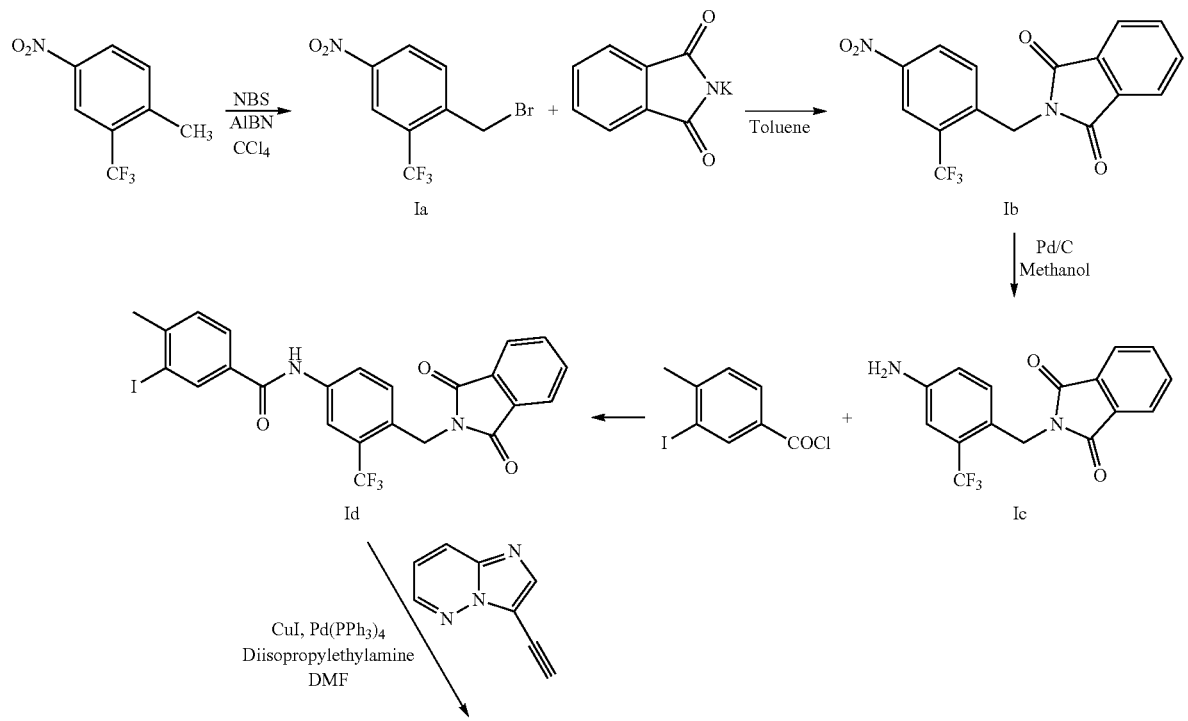

-continued
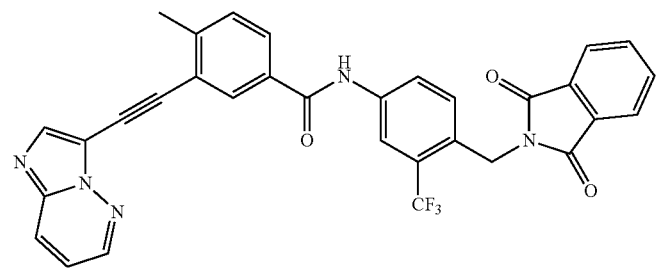
Ie
NH₂NH₂ | Methanol
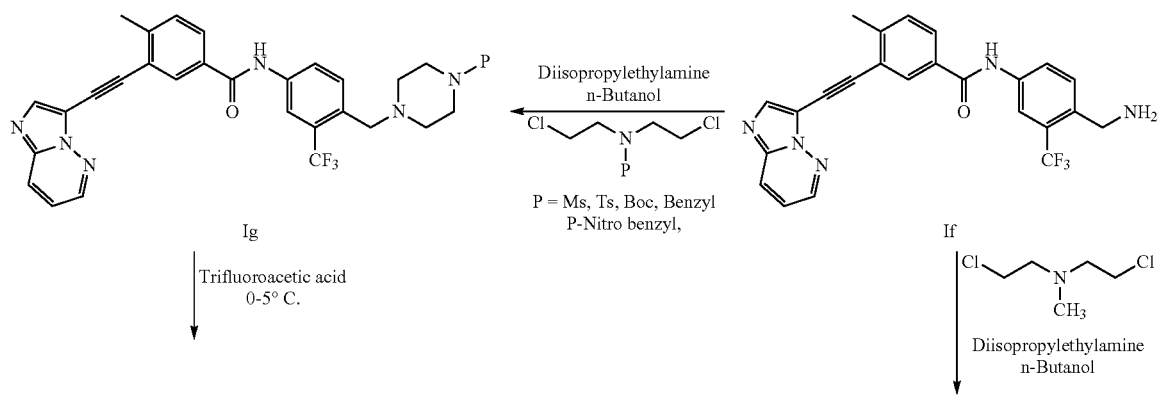
P = Ms, Ts, Boc, Benzyl, P-Nitro benzyl,
Ig | Trifluoroacetic acid 0-5° C.
If | Diisopropylethylamine n-Butanol
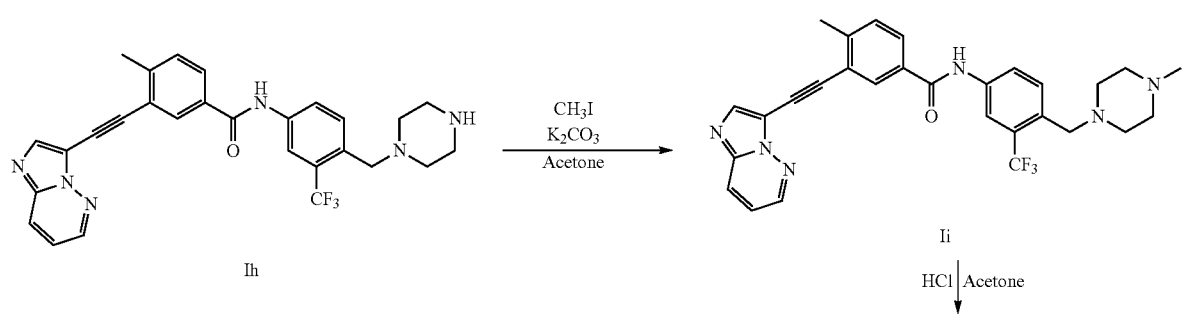
Ih | CH₃I K₂CO₃ Acetone → Ii
Ii | HCl Acetone
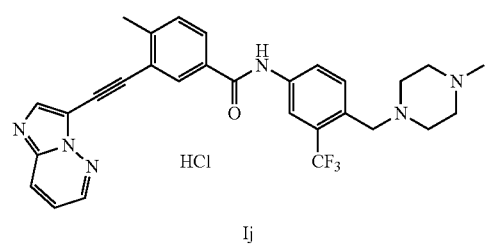
Ij SCHEME-II
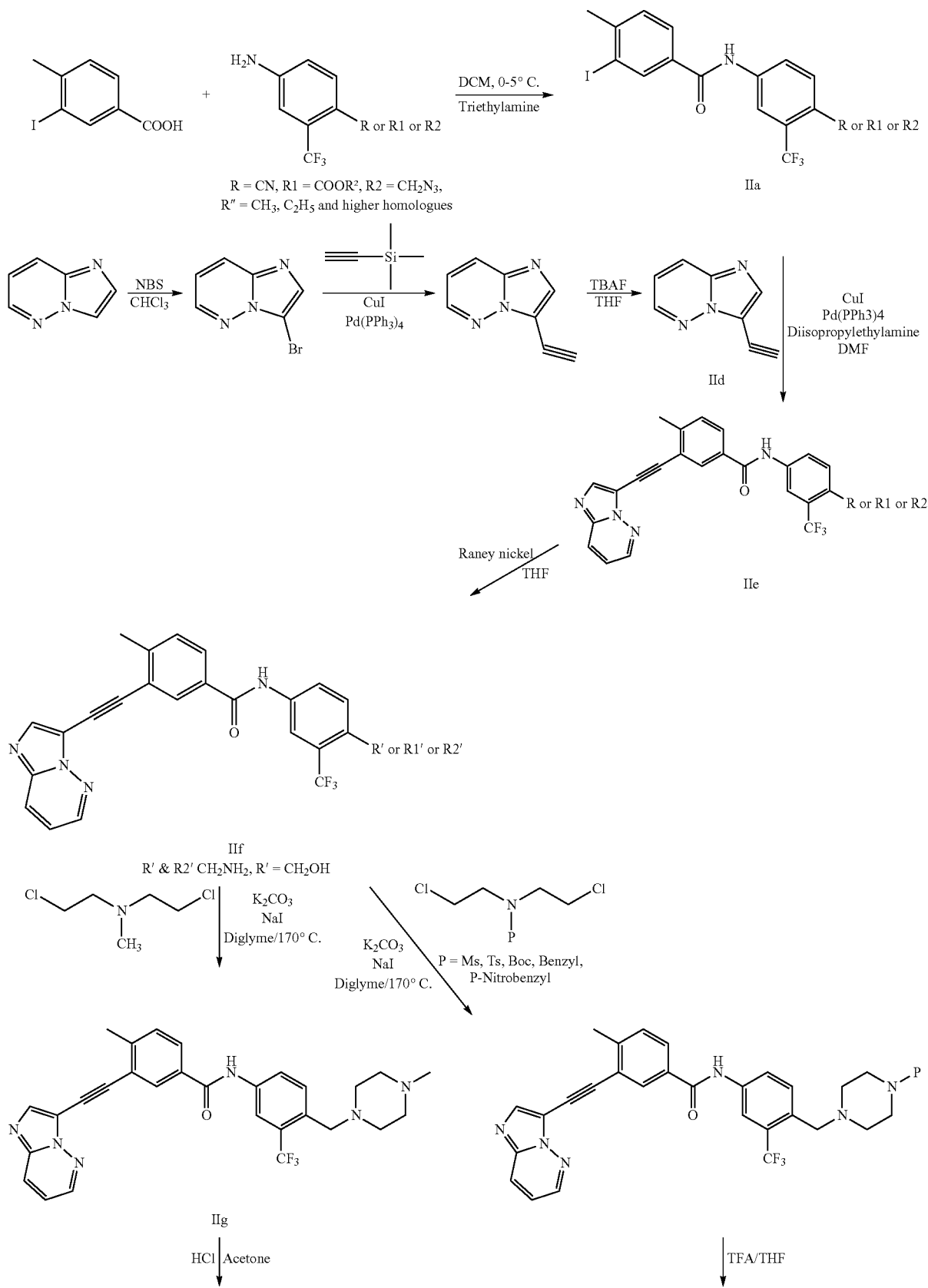

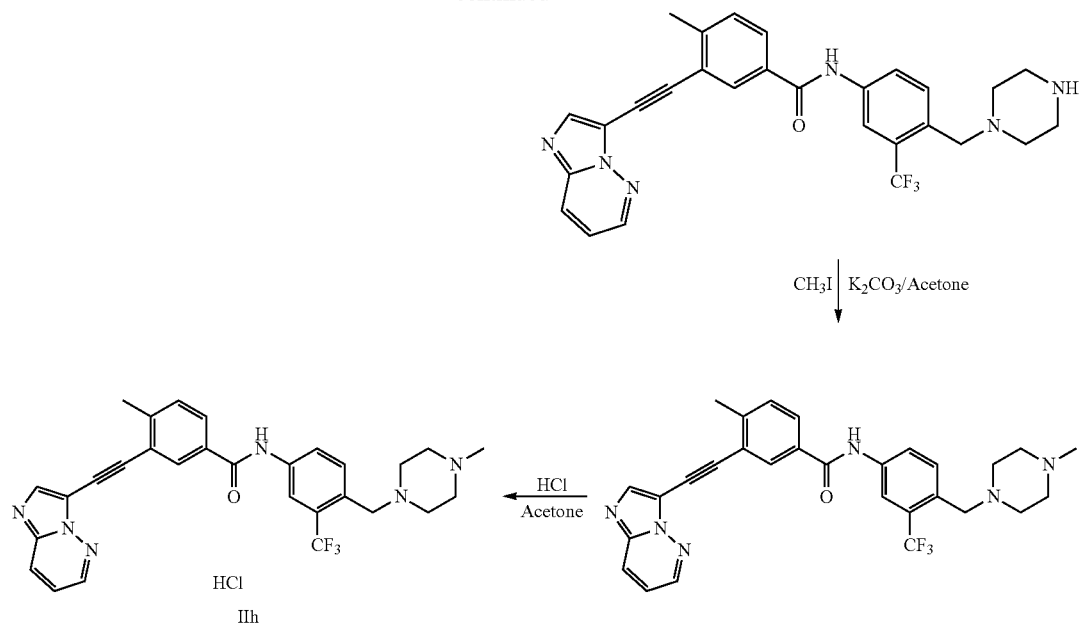
SCHEME-III
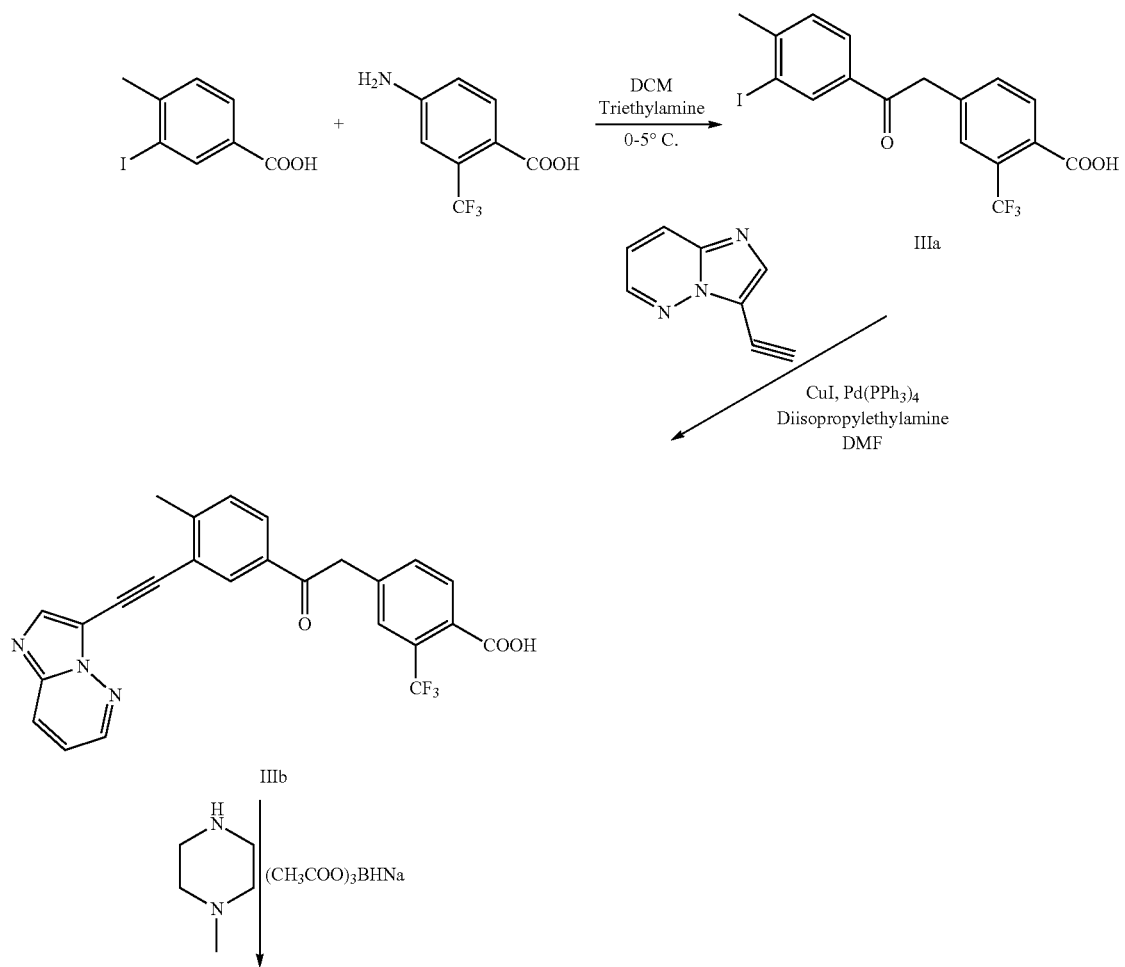

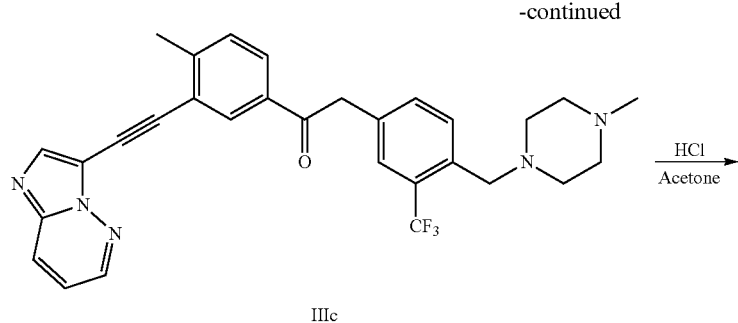
IIIc
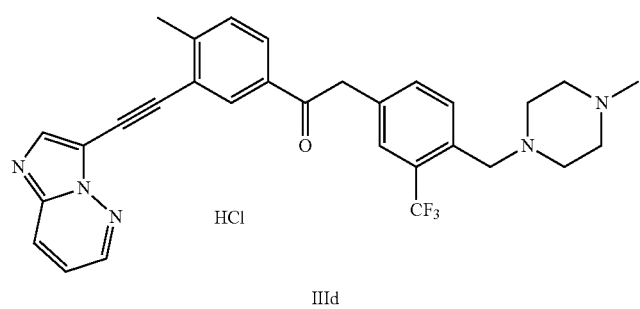
IIId
SCHEME-IV
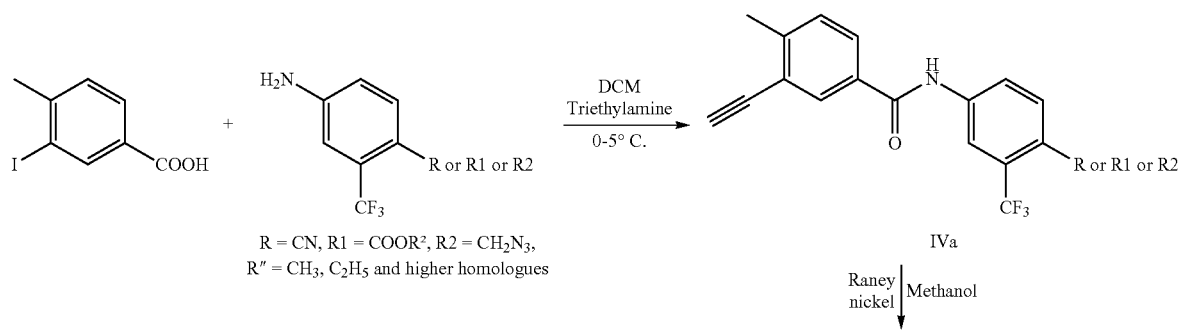
R = CN, R1 = COOR", R2 = CH$_2$N$_3$,
R" = CH$_3$, C$_2$H$_5$ and higher homologues
IVa
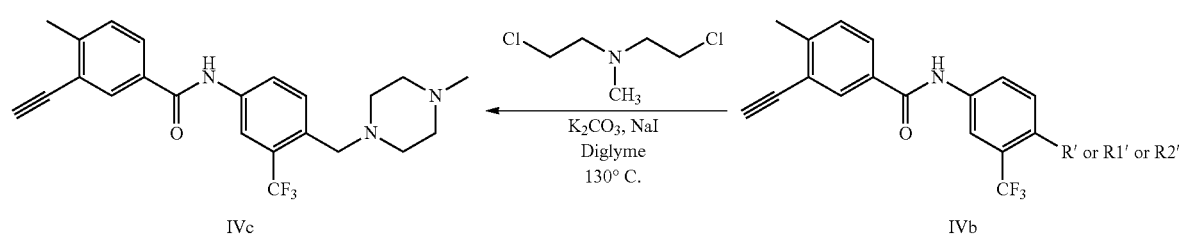
IVc
IVb
R' & R2' CH$_2$NH$_2$, R' = CH$_2$OH
P = Ms, Ts, Boc, Benzyl, P-Nitrobenzyl

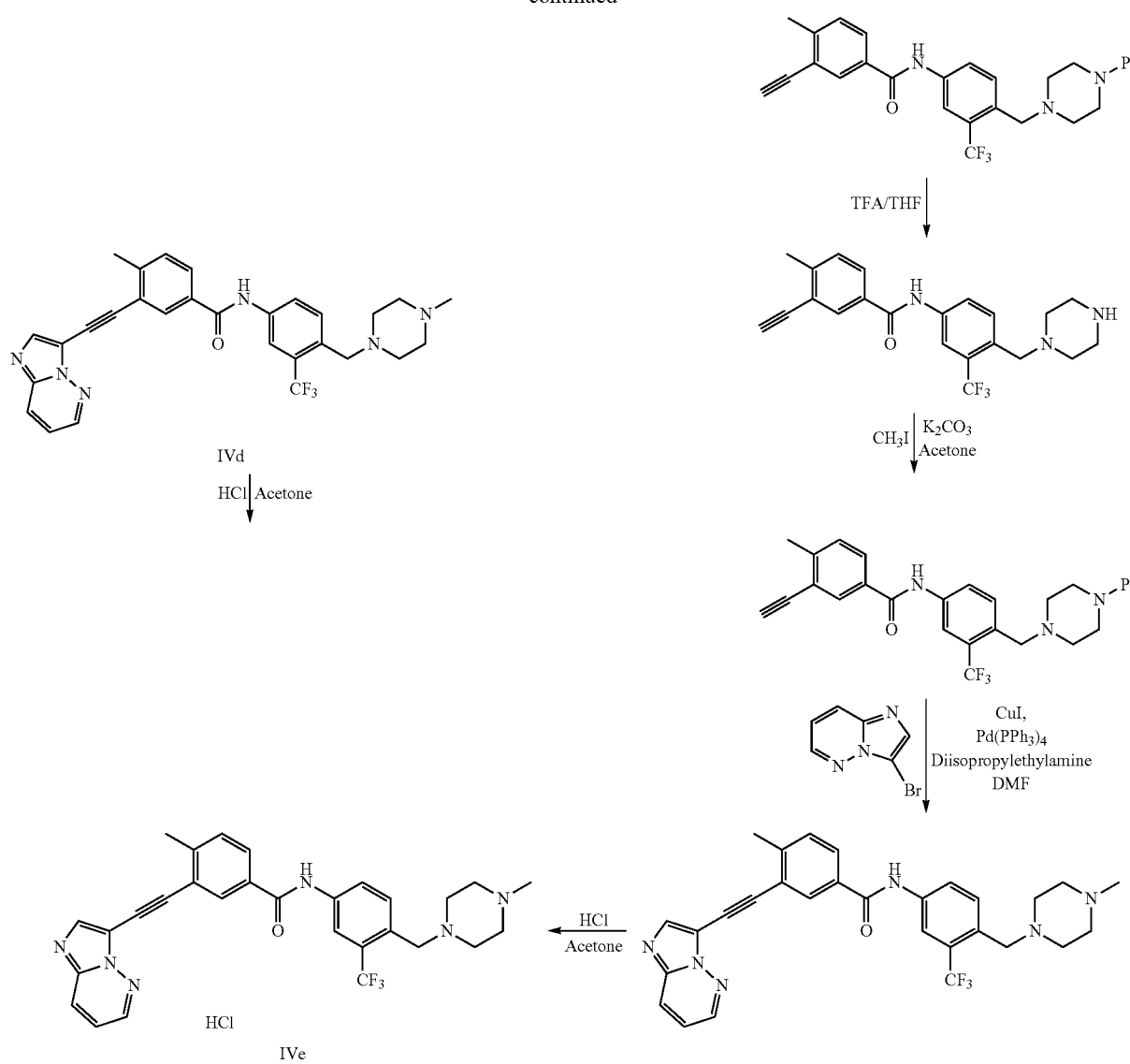
SCHEME-V
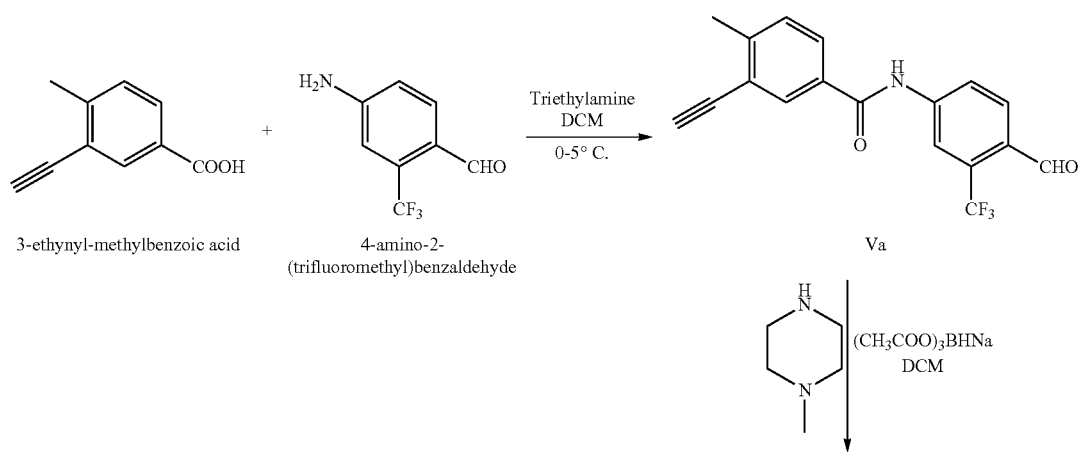
3-ethynyl-methylbenzoic acid + 4-amino-2-(trifluoromethyl)benzaldehyde → Va

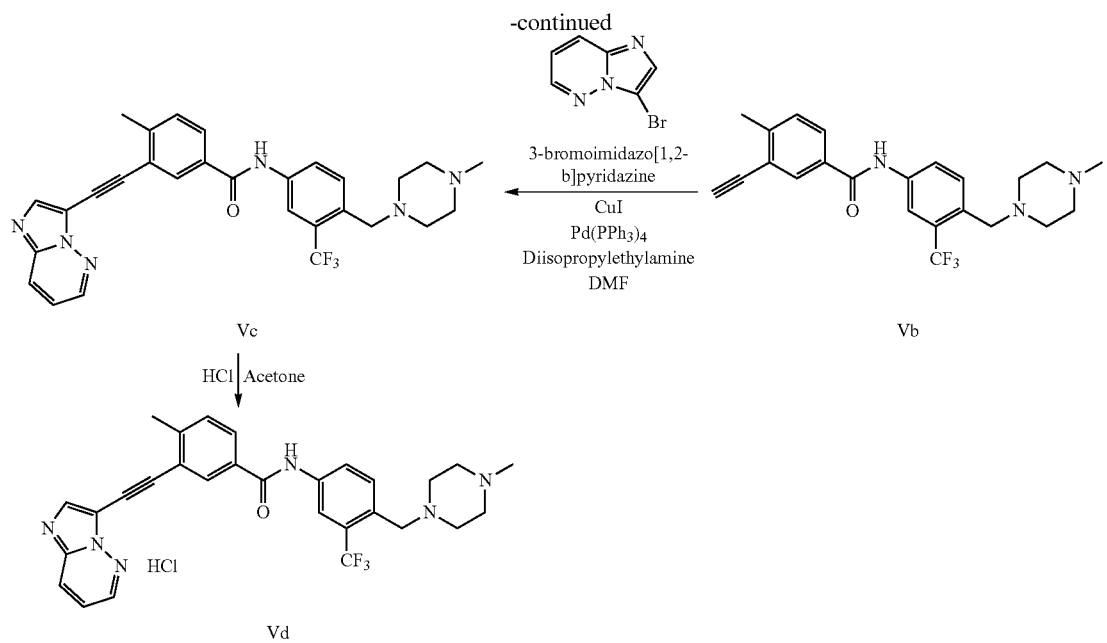

Scheme-I 1-(bromomethyl)-4-nitro-2-(trifluoromethyl)benzene (Compound Ia)

A suspension of 2-methyl-5-nitrobenzotrifluoride (3.90 g, 19 mmol), N-bromosuccinimide (NBS, 3.56 g, 20 mmol) and 2,2'-azobis(2-methylpropionitrile)(AIBN, 94 mg, 0.6 mmol) in $CCl_4$ (40 mL) was refluxed under nitrogen for 16 h. HPLC indicated ca. 50% conversion. More NBS (10 mmol) and AIBN (0.6 mmol) was added, and the mixture was refluxed for another 14 h. HPLC indicated ca. 80% conversion. The reaction mixture was cooled down, and the solid was filtered off and washed with ethyl acetate. The combined filtrate was washed with aq. $NaHCO_3$, dried over $Na_2SO_4$, filtered, concentrated on rotovap and further dried under vacuum to afford a solid (1-(bromomethyl)-4-nitro-2-(trifluoromethyl)benzene (Compound Ia)).

2-(4-nitro-2-(trifluoromethyl)benzyl)isoindoline-1,3-dione (Ib)

To a solution of 1-(bromomethyl)-4-nitro-2-(trifluoromethyl)benzene (Ia) (1.3 g, 4.69 mmol) in dimethylformamide, potassium phthalimide (1.9 g, 10.314 mmol) was added. The mixture was reacted overnight, extracted with ethyl acetate and washed by brine (3×20 mL). Drying over magnesium sulfate, evaporation of the solvent and purification by column chromatography (silica gel: 100-200 mesh, eluent:ethyl acetate/n-hexane) afforded 2-(4-nitro-2-(trifluoromethyl)benzyl)isoindoline-1,3-dione (1.6 g, 99%) (Ib).

2-(4-amino-2-(trifluoromethyl)benzyl)isoindoline-1,3-dione (Ic)

To a solution of 1,2-(4-nitro-2-(trifluoromethyl)benzyl)isoindoline-1,3-dione (Ib) (9.03 g, 32 mmol) in 95 ml methanol, 10% Pd on carbon (2.1 g, 30% by wt.) was charged under nitrogen. To this reaction mixture was passed a hydrogen gas and the mixture was stirred at room temperature for 22 hours or until complete as determined by TLC. To the reaction mixture ethyl acetate was added under argon. The product was filtered through Celite® filter agent and washed with a 1:1 solution of ethyl acetate and methanol. The filtrate was concentrated under reduced pressure to provide a solid (2-(4-amino-2-(trifluoromethyl)benzyl)isoindoline-1,3-dione (Ic)).

N-(4-((1,3-dioxoisoindolin-2-yl)methyl)-3-(trifluoromethyl)phenyl)-3-iodo-4-methylbenzamide (Id)

Oxalyl chloride (1.739 g, 1.20 ml, 13.7 mmol) was added dropwise to a solution of 3-iodo-4-methyl benzoic acid (0.717 mg, 2.74 mmol) and dichloromethane (9 ml). N,N-dimethylformamide (1 drop) was added and the colorless solution stirred at room temperature for 1 h. The solution was concentrated to afford 3-iodo-4-methyl benzoyl chloride as a light yellow solid which was used without purification. 2-(4-amino-2-(trifluoromethyl)benzyl)isoindoline-1,3-dione (Ic) (0.922 g, 2.88 mmol) was added to a solution of 3-iodo-4-methyl benzoyl chloride (0.767 g, 2.74 mmol) in dichloromethane (5 ml) and the mixture stirred at room temperature for 30 min. Triethylamine (0.360 g, 0.50 ml, 3.56 mmol) was added and the solution stirred at room temperature for 1 h. The reaction mixture was partitioned between dichloromethane and saturated aqueous sodium bicarbonate solution. The aqueous phase was separated and extracted with dichloromethane. The combined organic phases were washed with water, brine, dried over anhydrous sodium sulfate, filtered and concentrated to afford a solid (N-(4-((1,3-dioxoisoindolin-2-yl)methyl)-3-(trifluoromethyl)phenyl)-3-iodo-4-methylbenzamide (Id)).

N-(4-((1,3-dioxoisoindolin-2-yl)methyl)-3-(trifluoromethyl)phenyl)-3-(imidazo[1,2-b]pyridazin-3-ylethynyl)-4-methylbenzamide (Ie)

A mixture of 3-ethynylimidazo[1,2-a]pyridazine (0.075 g, 0.52 mmol), N-(4-((1,3-dioxoisoindolin-2-yl)methyl)-3-(trifluoromethyl)phenyl)-3-iodo-4-methylbenzamide (Id)

(0.293 g, 0.52 mmol), Pd(PPh$_3$)$_4$ (0.030 g, 0.026 mmol), copper iodide (0.007 g, 0.039 mmol), and diisopropylethylamine (0.14 mL (0.78 mmol) in 3.0 mL of DMF was stirred at ambient temperature overnight under an atmosphere of N$_2$. The reaction mixture was concentrated and the crude product was purified by silica gel flash chromatography to provide 0.081 g of product (N-(4-((1,3-dioxoisoindolin-2-yl)methyl)-3-(trifluoromethyl)phenyl)-3-(imidazo[1,2-b]pyridazin-3-ylethynyl)-4-methylbenzamide)(Ie).

N-(4-(aminomethyl)-3-(trifluoromethyl)phenyl)-3-(imidazo[1,2-b]pyridazin-3-ylethynyl)-4-methylbenzamide (If)

To a stirred solution of N-(4-((1,3-dioxoisoindolin-2-yl)methyl)-3-(trifluoromethyl)phenyl)-3-(imidazo[1,2-b]pyridazin-3-ylethynyl)-4-methylbenzamide (Ie) (3.08 g, 5.33 mmol) in tetrahydrofuran was added hydrazine monohydrate (4 equivalents). The mixture was stirred at reflux for 6 h, until complete consumption, as evidenced by TLC analysis. The mixture was cooled to room temperature. The mixture was treated with potassium bicarbonate to adjust the pH to 12-13. The mixture was extracted with ethyl acetate, washed by brine, dried over magnesium sulfate and concentrated under reduced pressure. The residue was purified by column chromatography (silica gel: 100-200 mesh, eluent: ethyl acetate/n-hexane) to afford the compound N-(4-(aminomethyl)-3-(trifluoromethyl)phenyl)-3-(imidazo[1,2-b]pyridazin-3-ylethynyl)-4-methylbenzamide (If) (1.8 g, 65%).

3-(imidazo[1,2-b]pyridazin-3-ylethynyl)-4-methyl-N-(4-((4-tosylpiperazin-1-yl)methyl)-3-(trifluoromethyl)phenyl)benzamide (Ig)

To a suspension of N-(4-(aminomethyl)-3-(trifluoromethyl)phenyl)-3-(imidazo[1,2-b]pyridazin-3-ylethynyl)-4-methylbenzamide (If) (3.22 g, 7.18 mmol) in diisopropylethylamine (2.49 mL, 14.32 mmol) was charged N,N-bis(2-chloroethyl)-4-toluenesulfonamide (2.13 g, 7.18 mmol). The reaction mixture was heated to reflux (~130° C.) for 36 h. The progress of the reaction was monitored by TLC. The reaction mixture was transferred into a mixture of deionized water (6 mL), ice (20 g), potassium carbonate (7 g), and dichloromethane (25 mL). The layers were separated and the aqueous layer extracted with dichloromethane (3×5 mL). The combined organic layers were treated with activated charcoal, dried over magnesium sulfate, and then evaporated to dryness under vacuum to give the product 3-(imidazo[1,2-b]pyridazin-3-ylethynyl)-4-methyl-N-(4-((4-tosylpiperazin-1-yl)methyl)-3-(trifluoromethyl)phenyl)benzamide (Ig) (2.2 g).

3-(imidazo[1,2-b]pyridazin-3-ylethynyl)-4-methyl-N-(4-(piperazin-1-ylmethyl)-3-(trifluoromethyl)phenyl)benzamide (Ih)

Trifluoroacetic acid (8.4 mL) was charged to a glass-lined reactor, efficient stirring was established, and the reaction mixture was cooled to 5° C. 3-(imidazo[1,2-b]pyridazin-3-ylethynyl)-4-methyl-N-(4-((4-tosylpiperazin-1-yl)methyl)-3-(trifluoromethyl)phenyl)benzamide (Ig) (7.73 g, 11.5 mmol) was charged in portions to the reactor, while keeping the internal temperature<20° C. Concentrated sulfuric acid (4.18 mL) was added slowly, controlling the exothermic acid-base reaction. The reaction mixture was heated to 75° C. and the reaction progress was monitored by TLC. Complete consumption of (<0.5%) was observed after 6 h. The reaction mixture was cooled to 5° C. and deionized water (33.0 mL) was charged while maintaining a temperature of <20° C. The pH of the solution was adjusted to 8.0 to 8.5 by addition of 10N aqueous sodium hydroxide while maintaining a temperature of <20° C. The aqueous layer was extracted with ethyl acetate (4×10.5 mL). The combined organic phases were washed with 1N NaOH (2×10.5 mL). The organic phase was returned to the reactor and the solvent was removed by distillation under reduced pressure, until 12-13 mL remained. Heptane (12.6 mL) was added and the solvent was removed by distillation under reduced pressure until 12-13 mL remained. Heptane (12.6 mL) was added and the solvent was removed by distillation under reduced pressure until 7 mL remained. The mixture was cooled to −10° C. and then aged at this temperature for 2 h. The solid (3-(imidazo[1,2-b]pyridazin-3-ylethynyl)-4-methyl-N-(4-(piperazin-1-ylmethyl)-3-(trifluoromethyl)phenyl)benzamide (Ih) was isolated by vacuum filtration.

3-(imidazo[1,2-b]pyridazin-3-ylethynyl)-4-methyl-N-(4-((4-methylpiperazin-1-yl)methyl)-3-(trifluoromethyl)phenyl)benzamide (Ii)

3-(imidazo[1,2-b]pyridazin-3-ylethynyl)-4-methyl-N-(4-(piperazin-1-ylmethyl)-3-(trifluoromethyl)phenyl)benzamide (Ih) (5.13 g) was dissolved in 100 ml of acetone and combined with 1.5 g of potassium carbonate. A solution of 1.45 g of methyl iodide in 20 ml of acetone was added dropwise into the suspension with stirring at 25° C. After stirring for 12 hours at 25° C., the mixture was filtered and the filtrate evaporated to dryness to yield ponatinib base (Ii).

3-(imidazo[1,2-b]pyridazin-3-ylethynyl)-4-methyl-N-(4-((4-methylpiperazin-1-yl)methyl)-3-(trifluoromethyl)phenyl)benzamide hydrochloride (Ij) (Ponatinib hydrochloride)

The residue (Ii) was taken up in acetone and hydrogen chloride gas introduced to afford 4.1 g of ponatinib hydrochloride (Ij) with purity>99.5% by HPLC method of analysis.

Scheme-II

N-(4-cyano-3-(trifluoromethyl)phenyl)-3-iodo-4-methylbenzamide (IIa)

Oxalyl chloride (1.739 g, 1.20 ml, 13.7 mmol) was added dropwise to a solution of 3-iodo-4-methyl benzoic acid (0.717 mg, 2.74 mmol) and dichloromethane (9 ml). N,N-Dimethylformamide (1 drop) was added and the colorless solution stirred at room temperature (RT) for 1 hour. The solution was concentrated to afford 3-iodo-4-methyl benzoyl chloride as light yellow solid which was used directly without purification. 3-iodo-4-methyl benzoyl chloride (0.767 g, 2.74 mmol) was added to a solution of 4-amino-2-(trifluoromethyl)benzonitrile (0.536 g, 2.88 mmol) and triethylamine (0.360 g, 0.50 ml, 3.56 mmol) in dichloromethane (5 ml) at 0-5° C. and the mixture stirred at room temperature for 1 hour. The reaction mixture was partitioned between dichloromethane and saturated aqueous sodium bicarbonate solution. The aqueous phase was separated and extracted with dichloromethane. The combined organic phases were washed with water, brine, dried over anhydrous sodium sulfate, filtered and concentrated to afford a product N-(4-cyano-3-(trifluoromethyl)phenyl)-3-iodo-4-methylbenzamide (IIa).

3-bromoimidazo[1,2-b]pyridazine (IIb)

A mixture of imidazo[1,2-b]pyridazine (2.0 g), N-bromosuccinimide (2.94 g), and chloroform (100 mL) was heated under reflux for 2 hr. Upon cooling, the solution was treated with a saturated aqueous solution of sodium carbonate (200 mL) and shaken. The chloroform layer was separated and concentrated to afford the compound 3-bromoimidazo[1,2-b]pyridazine (IIb).

3-((trimethylsilyl)ethynyl)imidazo[1,2-b]pyridazine (IIc)

A mixture of 3-bromoimidazo[1,2-b]pyridazine (IIb) (36.78 g, 0.186 mol), ethynyltrimethylsilane (21.89 g, 0.223 mol), Pd(PPh$_3$)$_4$ (10.73 g, 9.29 mmol), CuI (5.30 g, 0.028 mol), and diisopropylethylamine (32.4 mL, 0.279 mol) in 150 mL of DMF was stirred at ambient temperature, under an atmosphere of N$_2$, for 1 hour. The reaction mixture was concentrated and the crude product was purified by silica gel flash chromatography (eluted with 0-5% MeOH/DCM) to provide 28.46 g of 3-((trimethylsilyl)ethynyl)imidazo[1,2-b]pyridazine (IIc).

3-ethynylimidazo[1,2-b]pyridazine (IId)

To a solution of 3-((trimethylsilyl)ethynyl)imidazo[1.2-b]pyridazine (IIc) (28.46 g, 0.132 mol) in 200 mL of THF was added 145 mL (0.145 mol) of tetrabutylammonium fluoride (1.0 M in THF) at ambient temperature. The solution was stirred for 15 min, concentrated, and the crude product purified by silica gel flash chromatography (eluted with 0-5% MeOH/DCM) to provide 17.84 g of product (3-ethynylimidazo[1,2-b]pyridazine (IId)).

N-(4-cyano-3-(trifluoromethyl)phenyl)-3-(imidazo[1,2-b]pyridazin-3-ylethynyl)-4-methylbenzamide (IIe)

A mixture of 3-ethynylimidazo[1,2-a]pyridazine (IId) (0.075 g, 0.52 mmol), N-(4-cyano-3-(trifluoromethyl)phenyl)-3-iodo-4-methylbenzamide (IIa) (0.223 g, 0.52 mmol), Pd(PPh$_3$)$_4$ (0.030 g, 0.026 mmol), copper iodide (0.007 g, 0.039 mmol), and diisopropylethylamine (0.14 mL (0.78 mmol) in 3.0 mL of dimethylformamide was stirred at ambient temperature overnight under an atmosphere of N$_2$. The reaction mixture was concentrated and the crude product was purified by silica gel flash chromatography to provide 0.090 g of product (N-(4-cyano-3-(trifluoromethyl)phenyl)-3-(imidazo[1,2-b]pyridazin-3-ylethynyl)-4-methylbenzamide (IIe)).

N-(4-(aminomethyl)-3-(trifluoromethyl)phenyl)-3-(imidazo[1,2-b]pyridazin-3-ylethynyl)-4-methylbenzamide (IIf)

In a pressure reactor N-(4-cyano-3-(trifluoromethyl)phenyl)-3-(imidazo[1,2-b]pyridazin-3-ylethynyl)-4-methylbenzamide intermediate (IIe) (43.6 g, 98 mmol) was dissolved in anhydrous THF (940 mL), and the solution was purged with argon for 2-3 minutes, followed by the addition of 11 mL of the uniformly suspended catalyst (Raney® nickel 2400 catalyst suspension in water). After addition of a small amount of methanol to the suspension, the reactor was pressurized at 55 psi of H$_2$ while stirring vigorously. TLC monitoring of the reaction indicated a complete conversion of the starting material to the corresponding amine within 2.5 hours. The reaction mixture was filtered over a bed of Celite® filter agent and washed with 3×100 mL portions of anhydrous THF. The combined filtrates were evaporated to dryness, and further dried under high vacuum to afford product (N-(4-(aminomethyl)-3-(trifluoromethyl)phenyl)-3-(imidazo[1,2-b]pyridazin-3-ylethynyl)-4-methylbenzamide (IIf)).

3-(imidazo[1,2-b]pyridazin-3-ylethynyl)-4-methyl-N-(4-((4-methylpiperazin-1-yl)methyl)-3-(trifluoromethyl)phenyl)benzamide (Ig)

A mixture of N-(4-(aminomethyl)-3-(trifluoromethyl)phenyl)-3-(imidazo[1,2-b]pyridazin-3-ylethynyl)-4-methylbenzamide (IIf) (16.26 g, 0.036 mol) and bis(2-chloroethyl)methylamine hydrochloride (7 g) and potassium carbonate (5 g) in sodium iodide (2 g) in diglyme (150 m) was heated at 170° C. for 8 hours. The reaction was filtered and the filtrate was evaporated under high vacuum. The residue was mixed with ethyl acetate (200 ml) and water (200 ml) and extracted with ethyl acetate twice. The combined organic layer was washed with brine and dried over Na$_2$SO$_4$ and evaporated to give crude product (3-(imidazo[1,2-b]pyridazin-3-ylethynyl)-4-methyl-N-(4-((4-methylpiperazin-1-yl)methyl)-3-(trifluoromethyl)phenyl)benzamide (IIg)).

3-(imidazo[1,2-b]pyridazin-3-ylethynyl)-4-methyl-N-(4-((4-methylpiperazin-1-yl)methyl)-3-(trifluoromethyl)phenyl)benzamide hydrochloride (IIh) (Ponatinib hydrochloride)

3-(imidazo[1,2-b]pyridazin-3-ylethynyl)-4-methyl-N-(4-(piperazin-1-ylmethyl)-3-(trifluoromethyl)phenyl)benzamide (IIg) (4.0 g) was dissolved in 100 ml of acetone and dry hydrogen chloride was passed through the solution to afford 3.2 g of ponatinib hydrochloride with purity>99.5% by HPLC method of analysis. (IIh).

Scheme-III

N-(4-formyl-3-(trifluoromethyl)phenyl)-3-iodo-4-methylbenzamide (IIIa)

3-iodo-4-methyl benzoyl chloride (0.767 g, 2.74 mmol) was added to a solution of 4-amino-2-(trifluoromethyl)benzaldehyde (0.544 g, 2.88 mmol) and triethylamine (0.360 g, 0.50 ml, 3.56 mmol) in dichloromethane (5 ml) at 0-5° C. and the mixture stirred at room temperature for 1 hour. The reaction mixture was partitioned between dichloromethane and saturated aqueous sodium bicarbonate solution. The aqueous phase was separated and extracted with dichloromethane. The combined organic phases were washed with water, brine, dried over anhydrous sodium sulfate, filtered and concentrated to afford N-(4-formyl-3-(trifluoromethyl)phenyl)-3-iodo-4-methylbenzamide (IIIa).

N-(4-formyl-3-(trifluoromethyl)phenyl)-3-(imidazo[1,2-b]pyridazin-3-ylethynyl)-4-methylbenzamide (IIIb)

A mixture of 3-ethynylimidazo[1,2-a]pyridazine (IId) (0.075 g, 0.52 mmol), N-(4-formyl-3-(trifluoromethyl)phenyl)-3-iodo-4-methylbenzamide (IIIa) (0.225 g, 0.52 mmol), Pd(PPh$_3$)$_4$ (0.030 g, 0.026 mmol), copper iodide (0.007 g, 0.039 mmol), and diisopropylethylamine (0.14 mL (0.78 mmol) in 3.0 mL of dimethylformamide was stirred at ambient temperature overnight under an atmosphere of nitrogen. The reaction mixture was concentrated and the crude product was purified by silica gel flash chromatography to provide 0.078 g of product (N-(4-formyl-3-(trifluoromethyl)phenyl)-3-(imidazo[1,2-b]pyridazin-3-ylethynyl)-4-methylbenzamide (IIIb)).

3-(imidazo[1,2-b]pyridazin-3-ylethynyl)-4-methyl-N-(4-((4-methylpiperazin-1-yl)methyl)-3-(trifluoromethyl)phenyl)benzamide (IIIc)

Sodium triacetoxyborohydride (0.625 g, 1.25 mmol) was charged to a suspension of N-(4-formyl-3-(trifluoromethyl)phenyl)-3-(imidazo[1,2-b]pyridazin-3-ylethynyl)-4-methylbenzamide (IIIb) (1.18 g, 2.74 mmol), N-methylpiperazine (0.288 g, 2.88 mmol) and triethylamine (0.360 g, 0.50 ml, 3.56 mmol) in dichloromethane (5 ml) at room temperature and stirred overnight. Saturated aqueous sodium bicarbonate solution (2.5 ml) was added and the mixture stirred for 20-30 minutes. The phases were separated and the aqueous phase was washed with dichloromethane. The combined organics were washed with brine, dried and concentrated. Column chromatography eluting with ethyl acetate/hexane gave the title compound ponatinib (3-(imidazo[1,2-b]pyridazin-3-ylethynyl)-4-methyl-N-(4-((4-methylpiperazin-1-yl)methyl)-3-(trifluoromethyl)phenyl)benzamide (IIIc)).

3-(imidazo[1,2-b]pyridazin-3-ylethynyl)-4-methyl-N-(4-((4-methylpiperazin-1-yl)methyl)-3-(trifluoromethyl)phenyl)benzamide hydrochloride (IIId) (Ponatinib hydrochloride)

The solid ponatinib (3-(imidazo[1,2-b]pyridazin-3-ylethynyl)-4-methyl-N-(4-((4-methylpiperazin-1-yl)methyl)-3-(trifluoromethyl)phenyl)benzamide (IIIc)) (0.90 g) was dissolved in 10 ml of acetone and dry hydrogen chloride was passed through the solution to afford 0.65 g of ponatinib hydrochloride with purity>99.5% by HPLC method of analysis. (IIId).

Scheme-IV

3-ethynyl-4-methylbenzoic acid

Methyl 3-iodo-4-methylbenzoate (0.2 g, 0.724 mmol) was added with bis-triphenylphosphine-palladium dichloride (25.424 mg, 0.036 mmol) and copper (I) iodide in absolute THF (3 mL) and triethylamine (1 mL) under inert gas. Thereafter, trimethylsilyl-ethyne was added at RT and the mixture was stirred overnight. For working up, the mixture was diluted with ethyl acetate, poured onto 0.5M ammonia solution and the aqueous phase was extracted with ethyl acetate. The combined organic phases were washed with 0.5M hydrochloric acid and saturated sodium chloride solution, again extracted with ethyl acetate, dried over sodium sulfate, filtered and concentrated under reduced pressure. The residue was added with methanolic KOH (1 mL) and stirred for 2 hours at RT. The reaction mixture was diluted with ethyl acetate, poured onto 5% NaHCO$_3$ solution and extracted twice with ethyl acetate. The combined organic phases were washed with saturated sodium chloride solution, dried over sodium sulfate, filtered and concentrated under reduced pressure to afford 3-ethynyl-4-methylbenzoic acid.

3-ethynyl-4-methylbenzoyl chloride 3-ethynyl-4-methylbenzoic acid (2.0 g, 5.0 mmol) in SOCl$_2$ (12.5 mL) was heated under reflux for 1 hour. The volatiles were removed under reduced pressure. The residue was co-evaporated with toluene, and dried under vacuum to afford the desired chloride which was directly used in the next step without further purification.

N-(4-cyano-3-(trifluoromethyl)phenyl)-3-ethynyl-4-methylbenzamide (IVa)

3-ethynyl-4-methylbenzoyl chloride (0.489 g, 2.74 mmol) was added to a solution of 4-amino-2-(trifluoromethyl)benzonitrile (0.536 g, 2.88 mmol) and triethylamine (0.360 g, 0.50 ml, 3.56 mmol) in dichloromethane (5 ml) at 0-5° C. and the mixture stirred at room temperature for 1 hour. The reaction mixture was partitioned between dichloromethane and saturated aqueous sodium bicarbonate solution. The aqueous phase was separated and extracted with dichloromethane. The combined organic phases were washed with water and brine, dried over anhydrous sodium sulfate, filtered and concentrated to afford a product (N-(4-cyano-3-(trifluoromethyl)phenyl)-3-ethynyl-4-methylbenzamide (IVa)).

N-(4-(aminomethyl)-3-(trifluoromethyl)phenyl)-3-ethynyl-4-methylbenzamide (IVb)

In an autoclave reactor N-(4-cyano-3-(trifluoromethyl)phenyl)-3-ethynyl-4-methylbenzamide intermediate (IVa) (32.1 g, 98 mmol) was dissolved in methanol (963 mL), and the solution was purged with argon for 2-3 minutes, followed by the addition of 15 mL of the uniformly suspended catalyst (Raney® nickel 2400, suspension in water). After addition of a small amount of methanol to the suspension, the reactor was pressurized at 50 psi of H$_2$ while stirring vigorously. TLC monitoring of the reaction indicated a complete conversion of the starting material to the corresponding amine within 3 hours. The reaction mixture was filtered over a bed of Celite® filter agent and washed with 3×100 mL portions of methanol. The combined filtrates were evaporated to dryness, and further dried under high vacuum to afford product (N-(4-(aminomethyl)-3-(trifluoromethyl)phenyl)-3-ethynyl-4-methylbenzamide (IVb).

3-ethynyl-4-methyl-N-(4-((4-methylpiperazin-1-yl)methyl)-3-(trifluoromethyl)phenyl)benzamide (IVc)

A mixture of N-(4-(aminomethyl)-3-(trifluoromethyl)phenyl)-3-ethynyl-4-methylbenzamide (IVb) (11.9 g) and bis(2-chloroethyl)methylamine hydrochloride (7 g) and potassium carbonate (5 g) in sodium iodide (2 g) in diglyme (150 m) was heated at 130° C. for 8 hours. The reaction was filtered and the filtrate was evaporated under high vacuum. The residue was mixed with ethyl acetate (200 ml) and water (200 ml) and extracted with ethyl acetate twice. The combined organic layer was washed with brine and dried over Na$_2$SO$_4$ and evaporated to give crude product (3-ethynyl-4-methyl-N-(4-((4-methylpiperazin-1-yl)methyl)-3-(trifluoromethyl)phenyl)benzamide (IVc)).

3-(imidazo[1,2-b]pyridazin-3-ylethynyl)-4-methyl-N-(4-((4-methylpiperazin-1-yl)methyl)-3-(trifluoromethyl)phenyl)benzamide (IVd)

A mixture of 3-bromoimidazo[1,2-b]pyridazine (0.103 g, 0.52 mmol), 3-ethynyl-4-methyl-N-(4-((4-methylpiperazin- 1-yl)methyl)-3-(trifluoromethyl)phenyl)benzamide (IVc) (0.216 g, 0.52 mmol), Pd(PPh$_3$)$_4$ (0.030 g, 0.026 mmol), copper iodide (0.007 g, 0.039 mmol), and diisopropylethylamine (0.14 mL, 0.78 mmol) in 3.0 mL of dimethylformamide was stirred at ambient temperature overnight under an atmosphere of N$_2$. The reaction mixture was concentrated and the crude product was purified by silica gel flash chromatography to provide 0.14 g of 3-(imidazo[1,2-b]pyridazin-3-ylethynyl)-4-methyl-N-(4-((4-methylpiperazin-1-yl)methyl)-3-(trifluoromethyl)phenyl)benzamide (IVd).

3-(imidazo[1,2-b]pyridazin-3-ylethynyl)-4-methy-N-(4-((4-methylpiperazin-1-yl)methyl)-3-(trifluoromethyl)phenyl)benzamide hydrochloride (IVe) (Ponatinib hydrochloride)

3-(imidazo[1,2-b]pyridazin-3-ylethynyl)-4-methyl-N-(4-(piperazin-1-ylmethyl)-3-(trifluoromethyl)phenyl)benzamide (IVd) (4.0 g) was dissolved in 100 ml of acetone and dry hydrogen chloride was passed through the solution to afford 3.2 g of ponatinib hydrochloride (IVe) with purity>99.5% by HPLC method of analysis.

Scheme-V 3-ethynyl-N-(4-formyl-3-(trifluoromethyl)phenyl)-4-methylbenzamide (Va)

3-ethynyl-4-methylbenzoyl chloride (0.489 g, 2.74 mmol) was added to a solution of 4-amino-2-(trifluoromethyl) benzaldehyde (0.954 g, 2.88 mmol) and triethylamine (0.360 g, 0.50 ml, 3.56 mmol) in dichloromethane (5 ml) at 0-5° C. and the mixture stirred at room temperature for 1 hour. The reaction mixture was partitioned between dichloromethane and saturated aqueous sodium bicarbonate solution. The aqueous phase was separated and extracted with dichloromethane. The combined organic phases were washed with water, brine, dried over anhydrous sodium sulfate, filtered and concentrated to yield 3-ethynyl-N-(4-formyl-3-(trifluoromethyl)phenyl)-4-methylbenzamide (Va).

3-ethynyl-4-methyl-N-(4-((4-methylpiperazin-1-yl)methyl)-3-(trifluoromethyl)phenyl)benzamide (Vb)

Sodium triacetoxyborohydride (0.625 g, 1.25 mmol) was charged to a suspension of 3-ethynyl-N-(4-formyl-3-(trifluoromethyl)phenyl)-4-methylbenzamide (Va) (0.90 g, 2.74 mmol), N-methylpiperazine (0.288 g, 2.88 mmol) and triethylamine (0.360 g, 0.50 ml, 3.56 mmol) in dichloromethane (5 ml) at room temperature and stirred overnight. Saturated aqueous sodium bicarbonate solution (2.5 ml) was added and the mixture stirred for 20-30 minutes. The phases were separated and the aqueous phase was washed with dichloromethane. The combined organics were washed with brine, dried and concentrated to afford 3-ethynyl-4-methyl-N-(4-((4-methylpiperazin-1-yl)methyl)-3-(trifluoromethyl) phenyl)benzamide (Vb).

3-(imidazo[1,2-b]pyridazin-3-ylethynyl)-4-methyl-N-(4-((4-methylpiperazin-1-yl)methyl)-3-(trifluoromethyl)phenyl)benzamide (Vc)

A mixture of 3-bromoimidazo[1,2-b]pyridazine (0.103 g, 0.52 mmol), 3-ethynyl-4-methyl-N-(4-((4-methylpiperazin-1-yl)methyl)-3-(trifluoromethyl)phenyl)benzamide (Vb) (0.216 g, 0.52 mmol), Pd(PPh$_3$)$_4$ (0.030 g, 0.026 mmol), copper iodide (0.007 g, 0.039 mmol), and diisopropylethylamine (0.14 mL, 0.78 mmol) in 3.0 mL of dimethylformamide was stirred at ambient temperature overnight under an atmosphere of N$_2$. The reaction mixture was concentrated and the crude product was purified by silica gel flash chromatography to provide 0.14 g of 3-(imidazo[1,2-b]pyridazin-3-ylethynyl)-4-methyl-N-(4-((4-methylpiperazin-1-yl)methyl)-3-(trifluoromethyl)phenyl)benzamide (Vc).

3-(imidazo[1,2-b]pyridazin-3-ylethynyl)-4-methyl-N-(4-((4-methylpiperazin-1-yl)methyl)-3-(trifluoromethyl)phenyl)benzamide hydrochloride (Vd) (Ponatinib hydrochloride)

3-(imidazo[1,2-b]pyridazin-3-ylethynyl)-4-methyl-N-(4-(piperazin-1-ylmethyl)-3-(trifluoromethyl)phenyl)benzamide (Vc) (4.0 g) was dissolved in 100 ml of acetone and dry hydrogen chloride was passed through the solution to afford 3.2 g of ponatinib hydrochloride (Vd) with purity>99.5% by HPLC method of analysis.

Although the compositions and methods of the present disclosure have been described with reference to exemplary embodiments thereof, the present disclosure is not limited thereby. Indeed, the exemplary embodiments are implementations of the disclosed compositions and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

What is claimed is:

1. A method for the production of ponatinib hydrochloride of the formula (I)

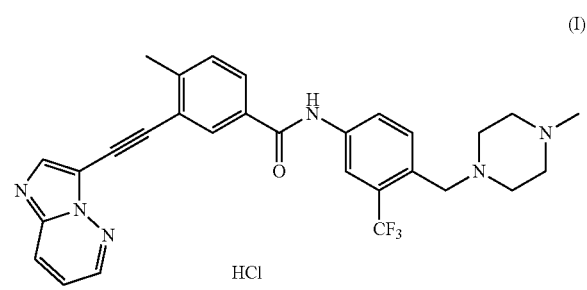 [SMILES: Cc1ccc(C(=O)Nc2ccc(CN3CCN(C)CC3)c(C(F)(F)F)c2)cc1C#Cc1cnc2cccnn12 ; Cl]

comprising reacting a compound of formula (II) 1-(halomethyl)-4-nitro-2-(trifluoromethyl)benzene

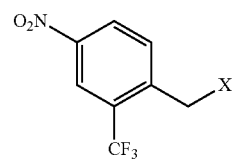

wherein X is a halogen, with potassium phthalimide

to obtain a phthalimide derivative having the formula Ib

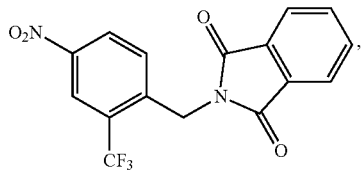

catalytically hydrogenating the phthalimide derivative of formula Ib to obtain a compound having the formula Ic

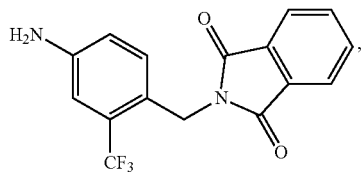

reacting the compound of formula Ic with 3-iodo-4-methylbenzoyl chloride having the formula

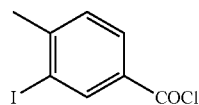

to obtain N-(4-((1,3-dioxoisoindolin-2-yl)methyl)-3-(trifluoromethyl)phenyl)-3-iodo-4-methylbenzamide having the formula Id

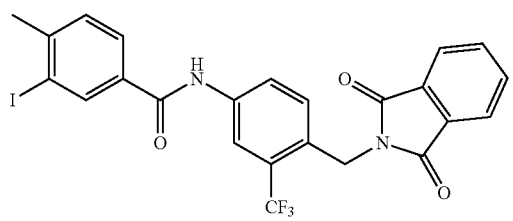

reacting the compound of formula Id with 3-ethynylimidazo[1,2-b]pyridazine in a coupling reaction to obtain a compound of the formula Ie

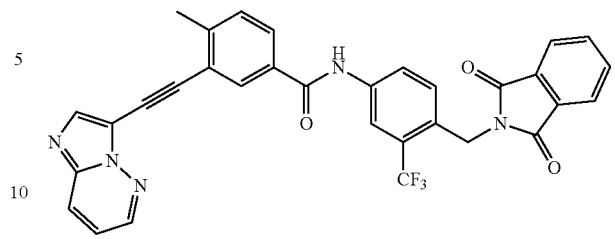

subjecting the compound of formula Ie to hydrolysis to obtain N-(4-(aminomethyl)-3-(trifluoromethyl)phenyl)-3-(imidazo[1,2-b]pyridazin-3-ylethynyl)-4-methylbenzamide, subsequently forming a piperazine ring by treatment of the N-(4-(aminomethyl)-3-(trifluoromethyl)phenyl)-3-(imidazo[1,2-b]pyridazin-3-ylethynyl)-4-methylbenzamide with
a) 2-chloro-N-(2-chloroethyl)-N-methylethanamine; or
b) a 2-chloro-N-(2-chloroethyl)-N-substituted derivative of the formula (VI)

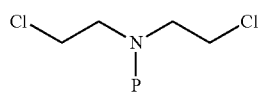

wherein P is a protecting group, wherein when the piperazine ring is formed using a) 2-chloro-N-(2-chloroethyl)-N-methylethanamine, subsequently forming the ponatinib hydrochloride using hydrogen chloride; and
wherein when the piperazine ring is formed using b) 2-chloro-N-(2-chloroethyl)-N-substituted derivative of the formula (VI), subsequently deprotecting the piperazine ring to obtain a compound having the formula Ih

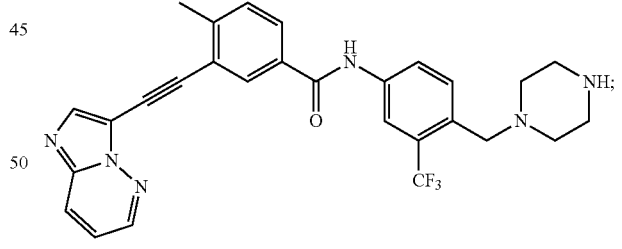

methylating compound Ih and subsequently forming the ponatinib hydrochloride using hydrogen chloride.

2. The method according to claim 1 wherein X is Br.

3. The method according to claim 1 wherein P is tosyl, mesyl, carboxybenzyl, benzyl, nitro benzyl or amino.

4. The method according to claim 1 wherein the step of methylating the compound of formula Ih comprises N-methylation with methyl iodide.

5. The method according to claim 1 wherein the step of forming a piperazine ring comprises treatment of the N-(4-(aminomethyl)-3-(trifluoromethyl)phenyl)-3-(imidazo[1,2-b]pyridazin-3-ylethynyl)-4-methylbenzamide with 2-chloro-N-(2-chloroethyl)-N-methylethanamine.

6. The method according to claim 1 wherein the step of forming a piperazine ring comprises treatment of the N-(4-(aminomethyl)-3-(trifluoromethyl)phenyl)-3-(imidazo[1,2-b]pyridazin-3-ylethynyl)-4-methylbenzamide with a 2-chloro-N-(2-chloroethyl)-N-substituted derivative of the formula (VI) wherein P is a protecting group and subsequently deprotecting the piperazine ring.

7. The method according to claim 1 wherein the step of deprotection of the piperazine ring is carried out using an acid.

8. The method according to claim 7 wherein the acid is selected from the group consisting of concentrated sulfuric acid, HBr in acetic acid, HBr in water and trifluoroacetic acid.

* * * * *